United States Patent
Kesten et al.

(10) Patent No.: US 10,183,153 B2
(45) Date of Patent: Jan. 22, 2019

(54) SINUS WALL IMPLANT

(71) Applicant: Acclarent, Inc., Irvine, CA (US)

(72) Inventors: Randy J. Kesten, Mountain View, CA (US); Thomas R. Jenkins, Alameda, CA (US); Jessica M. Liberatore, San Mateo, CA (US)

(73) Assignee: Acclarent, Inc., Irvine, CA (US)

( * ) Notice: Subject to any disclaimer, the term of this patent is extended or adjusted under 35 U.S.C. 154(b) by 352 days.

(21) Appl. No.: 15/204,208

(22) Filed: Jul. 7, 2016

(65) Prior Publication Data

US 2016/0310712 A1    Oct. 27, 2016

Related U.S. Application Data

(63) Continuation of application No. 14/483,186, filed on Sep. 11, 2014, now Pat. No. 9,433,763.
(Continued)

(51) Int. Cl.
*A61M 27/00* (2006.01)
*A61M 31/00* (2006.01)
(Continued)

(52) U.S. Cl.
CPC ....... *A61M 27/002* (2013.01); *A61F 13/2005* (2013.01); *A61F 13/2051* (2013.01);
(Continued)

(58) Field of Classification Search
CPC ........ A61F 2013/530868; A61F 13/53; A61M 27/002; A61M 2210/0618; A61M 16/0666; A61M 31/00; A61M 31/002
See application file for complete search history.

(56) References Cited

U.S. PATENT DOCUMENTS

| 4,233,025 A | 11/1980 | Larson et al. |
| 4,249,531 A | 2/1981 | Heller et al. |

(Continued)

FOREIGN PATENT DOCUMENTS

| EP | 0467516 | 1/1992 |
| EP | 0605974 | 7/1994 |
| WO | WO 92/15286 | 9/1992 |

OTHER PUBLICATIONS

Shikani, A. "A New Middle Meatal Anstrostomy Stent for Functional Endoscopic Sinus Surgery", *Laryngoscope*. May 1994, 104 p. 638-641.
(Continued)

*Primary Examiner* — Leslie Deak
(74) *Attorney, Agent, or Firm* — Frost Brown Todd LLC

(57) ABSTRACT

An apparatus comprises an absorbent body, a non-permeable feature, and a port feature. The absorbent body comprises a wicking feature. The non-permeable feature is coupled with the absorbent body. The non-permeable feature and at least a portion of the absorbent body are configured to fit in an opening in a paranasal sinus wall. The port feature extends through the absorbent body. The port feature defines a lumen. The wicking feature extends outwardly relative to the port lumen. During installation of the apparatus, the non-permeable feature is positioned in an opening in the paranasal sinus wall. The absorbent body is oriented such that the wicking feature is in contact with mucosal tissue in a sinus cavity defined by the paranasal sinus wall. A proximal portion of the absorbent body is positioned outside the paranasal sinus wall.

20 Claims, 19 Drawing Sheets

Related U.S. Application Data

(60) Provisional application No. 61/883,234, filed on Sep. 27, 2013.

(51) Int. Cl.
*A61F 13/53* (2006.01)
*A61F 13/20* (2006.01)
*A61F 13/537* (2006.01)

(52) U.S. Cl.
CPC ............ *A61F 13/53* (2013.01); *A61F 13/537* (2013.01); *A61M 27/00* (2013.01); *A61M 31/00* (2013.01); *A61M 31/002* (2013.01); *A61F 2013/530868* (2013.01); *A61M 27/008* (2013.01); *A61M 2210/0681* (2013.01)

(56) References Cited

U.S. PATENT DOCUMENTS

| | | |
|---|---|---|
| 4,755,171 A | 7/1988 | Tennant |
| 5,195,984 A | 3/1993 | Schatz |
| 5,203,699 A | 4/1993 | McGuire |
| 5,211,952 A | 5/1993 | Spicer et al. |
| 5,234,456 A | 8/1993 | Silvestrini |
| 5,246,455 A | 9/1993 | Shikani |
| 5,376,376 A | 12/1994 | Li |
| 5,443,458 A | 8/1995 | Eury |
| 5,693,065 A | 12/1997 | Rains |
| 5,741,333 A | 4/1998 | Frid |
| 5,824,049 A | 10/1998 | Ragheb et al. |
| 5,827,224 A | 10/1998 | Shippert |
| 6,652,575 B2 | 11/2003 | Wang |
| 8,025,635 B2 | 9/2011 | Eaton et al. |
| 8,195,984 B2 | 6/2012 | Alberi et al. |
| 8,740,929 B2 | 6/2014 | Gopferich et al. |
| 9,155,492 B2 | 10/2015 | Jenkins et al. |
| 9,433,763 B2 | 9/2016 | Kesten et al. |
| 2008/0243140 A1 | 10/2008 | Gopferich et al. |
| 2010/0030031 A1 | 2/2010 | Goldfarb et al. |
| 2010/0274204 A1 | 10/2010 | Rapacki et al. |
| 2011/0004057 A1 | 1/2011 | Goldfarb et al. |
| 2014/0074141 A1 | 3/2014 | Johnson et al. |
| 2014/0277039 A1 | 9/2014 | Liberatore et al. |

OTHER PUBLICATIONS

U.S. Appl. No. 61/883,234, filed Sep. 27, 2013.
International Search Report and Written Opinion dated Jan. 5, 2015 for Application No. PCT/US2014/056265.

SINUS WALL IMPLANT

PRIORITY

This application is a continuation application of U.S. Nonprovisional patent application Ser. No. 14/483,186, entitled "Sinus Wall Implant," filed Sep. 11, 2014, issued as U.S. Pat. No. 9,433,186 on Sep. 6, 2016, which claims priority to U.S. Provisional Pat. App. No. 61/883,234, entitled "Sinus Wall Implant," filed Sep. 27, 2013, the disclosure of which is incorporated by reference herein.

BACKGROUND

In some instances, it may be desirable to implant a device within or adjacent to a wall of a patient's paranasal sinus. Paranasal sinuses include ostia for providing fluid communication to and from the sinus and the nasal cavity. In particular, such ostia may provide paths for communication of mucus from the sinus to the nasal cavity; and of air/medication/etc. from the nasal cavity to the sinus. In some instances, it may be desirable to provide an implant that promotes or enhances the communication of mucus from the sinus to the nasal cavity, that promotes or enhances the communication of air from the nasal cavity to the sinus, and/or that promotes or enhances the communication of medication or other substances from the nasal cavity to the sinus.

If a naturally occurring ostium is blocked, functionally closed due to mucosal thickening, or otherwise not sufficiently open, the ostium may be dilated before deploying an implant in the ostium. One method of dilating an ostium includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. Examples of such dilation systems are disclosed in U.S. Pub. No. 2011/0004057, now abandoned, entitled "Systems and Methods for Transnasal Dilation of Passageways in the Ear, Nose or Throat," published Jan. 6, 2011, the disclosure of which is incorporated by reference herein. Another example of such a system is the Relieva® Spin Balloon Sinuplasty™ System by Acclarent, Inc. of Menlo Park, Calif. Exemplary balloon dilator catheters include the Relieva Ultirra™ Sinus Balloon Catheter and the, both by Acclarent, Inc. of Menlo Park, Calif. An exemplary guide catheter that may be used to position a balloon catheter is the Relieva Flex™ Sinus Guide Catheter by Acclarent, Inc. of Menlo Park, Calif. Examples of devices that may be used to inflate a balloon of a dilation catheter are disclosed in U.S. patent application Ser. No. 14/020,924, titled "Inflator for Dilation of Anatomical Passageway," filed Sep. 9, 2013, published as U.S. Pat. Pub. No. 2014/0074141 on Mar. 13, 2014, issued as U.S. Pat. No. 9,962,530 on May 8, 2018, the disclosure of which is incorporated by reference herein.

In some instances, it may be desirable to create an ostium in a sinus. This may be done with a cutting device that is operable to cut through bone and tissue or otherwise form an opening in a sinus wall. Examples of such devices are disclosed in U.S. patent application Ser. No. 14/038,867, entitled "Apparatus and Method for Treatment of Ethmoid Sinusitis," filed on Sep. 27, 2013, published as U.S. Pat. Pub. No. 2014/0277039 on Sep. 18, 2014, now abandoned, the disclosure of which is incorporated by reference herein. When an ostium is formed using a cutting device, the ostium may be further enlarged by a balloon dilation device or using other devices/techniques.

A variable direction view endoscope may be used to provide visualization within the nasal cavity to position a dilation catheter, a cutting device, and/or an implant at a desired location. A variable direction view endoscope may enable viewing along a variety of transverse viewing angles without having to flex the shaft of the endoscope within the nasal cavity. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif. In some instances where a balloon dilation catheter is used, an illuminating guidewire may also be used to provide confirmation of the proper positioning of the catheter before inflating the balloon. Such a guidewire may be positioned within the target area and then illuminated, with light projecting from the distal end of the guidewire. This light may illuminate the adjacent tissue and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

While several instruments and procedures have been made and used for treatment of anatomical passageways in a patient, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
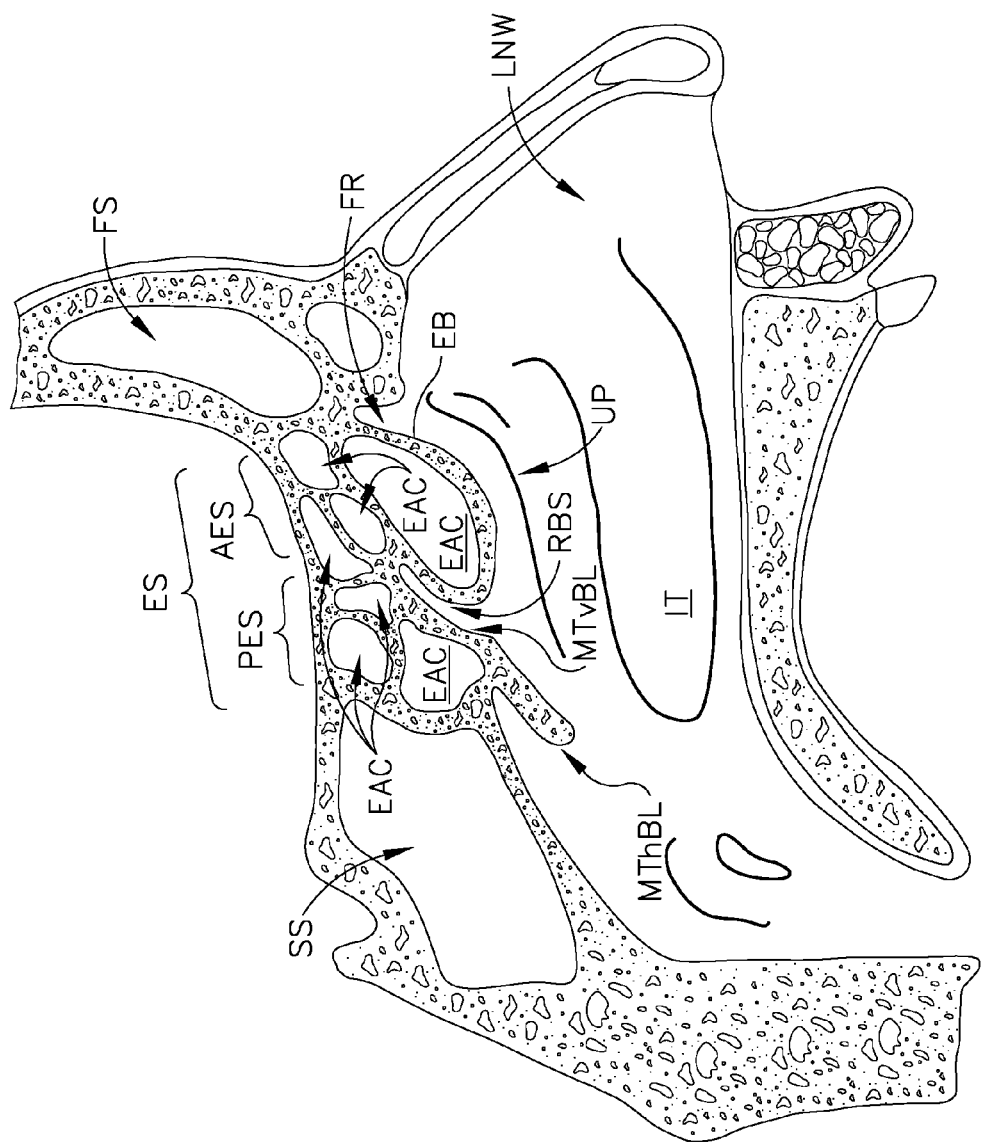
FIG. 1 depicts a left sagittal cross-sectional view of a portion of a human head, showing paranasal sinus structures.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. OVERVIEW OF SINUS SYSTEM

Figure 2:
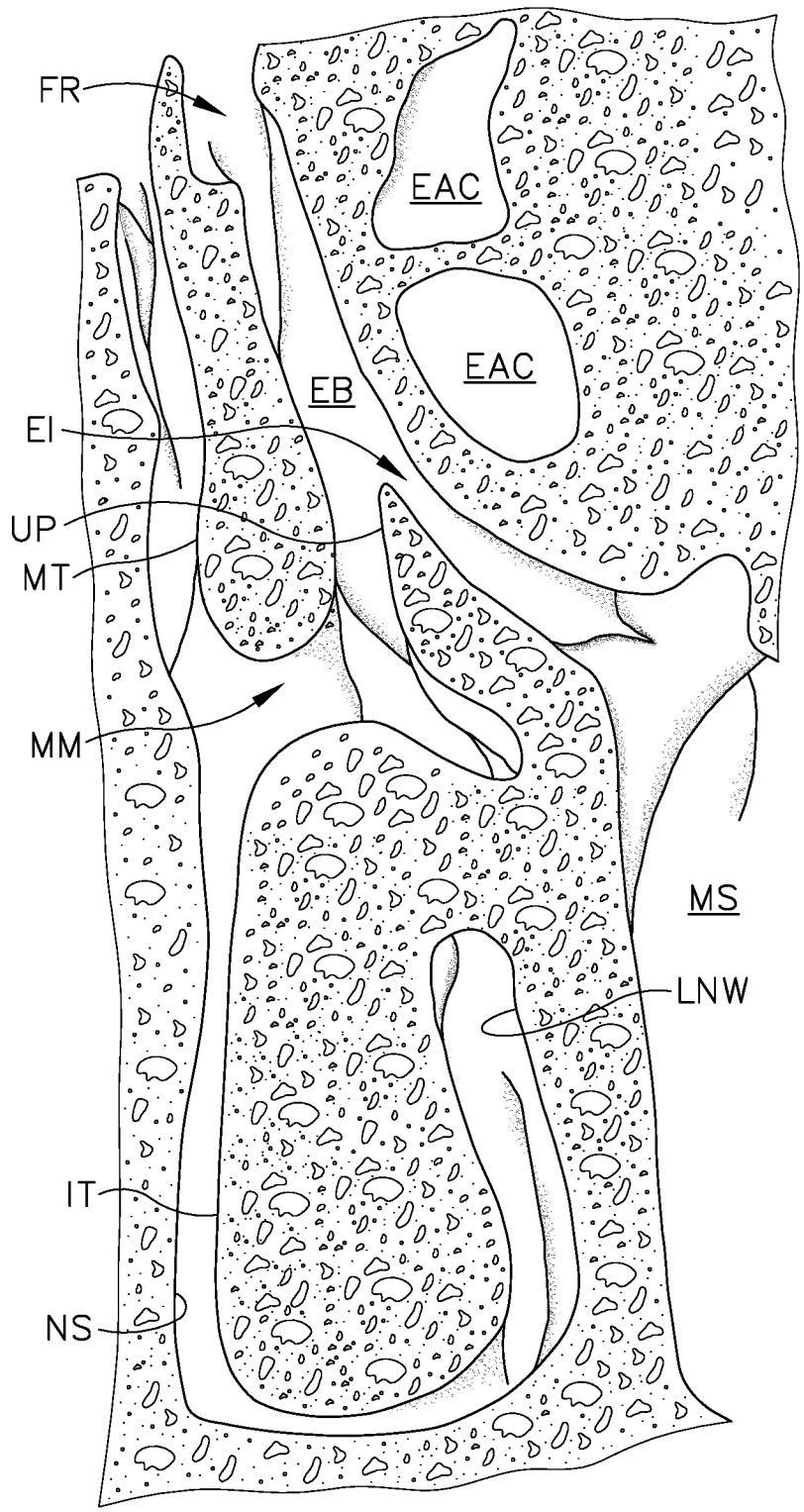
FIG. 2 depicts an anterior coronal cross-sectional view of a portion of a human head, showing paranasal sinus structures.
Figure 3:
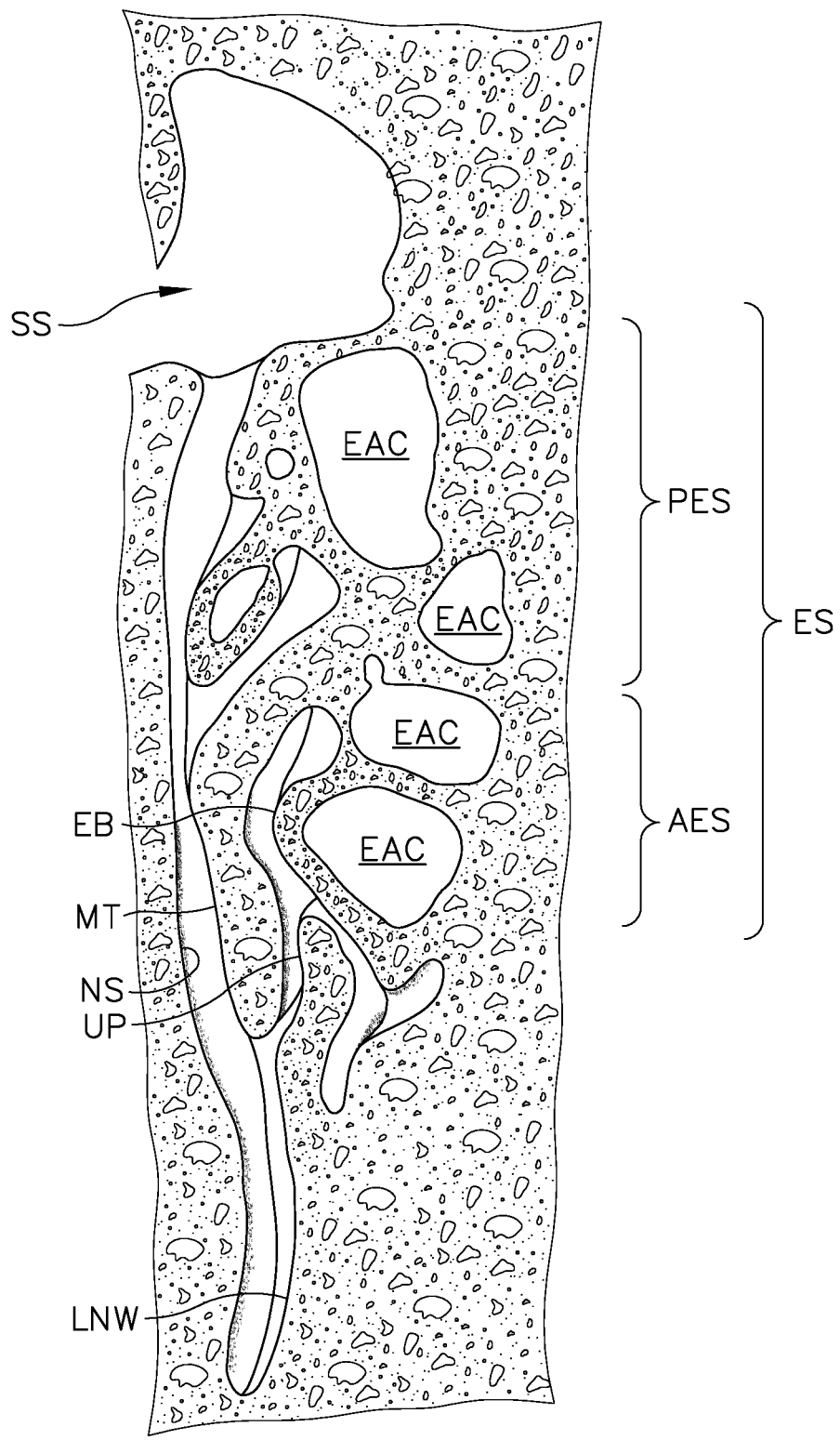
FIG. 3 depicts a superior axial cross-sectional view of a portion of a human head, showing paranasal sinus structures.
Figure 4:
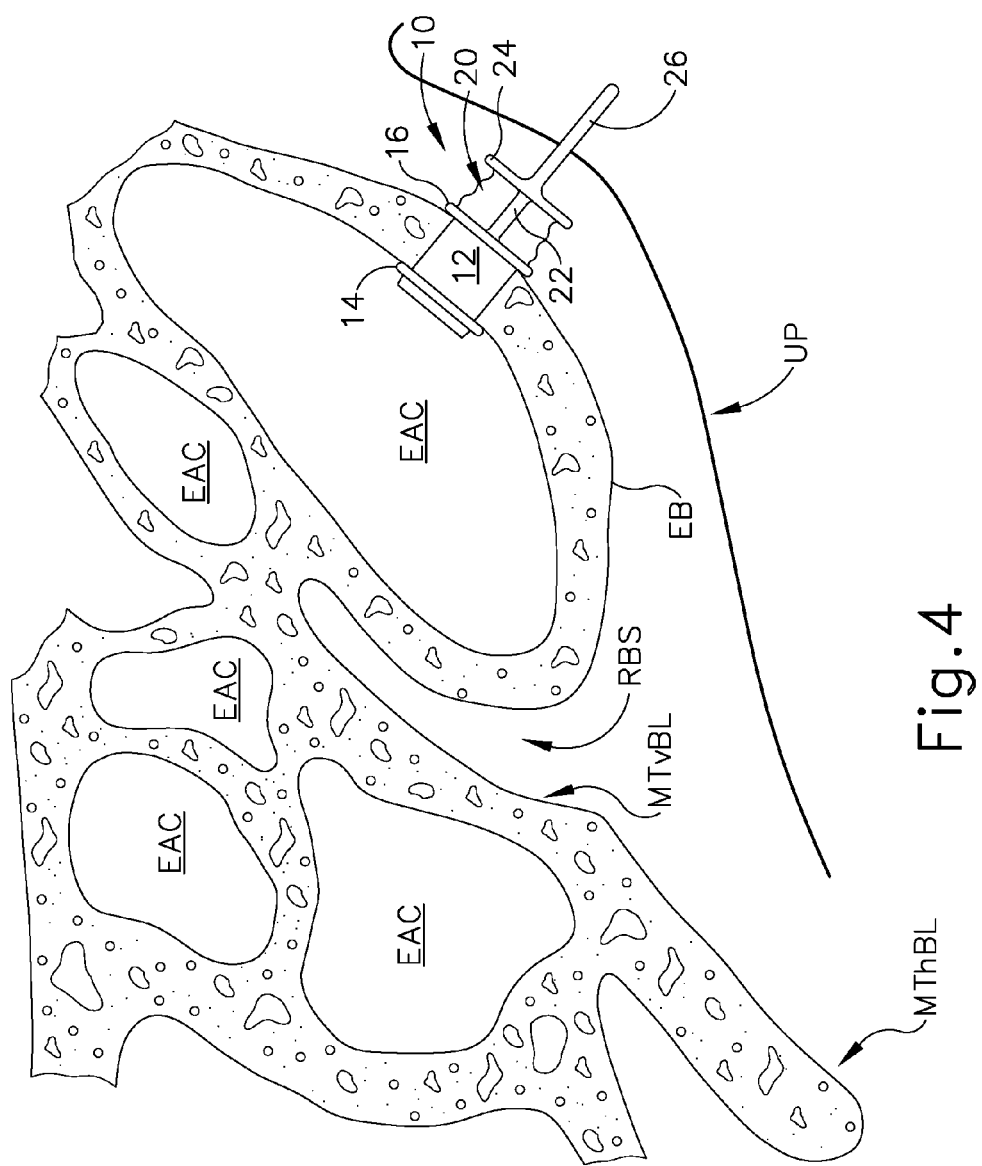
FIG. 4 depicts an enlarged left sagittal cross-sectional view of a portion of a human head, showing an implant positioned in the ethmoid bulla.
Figure 5:
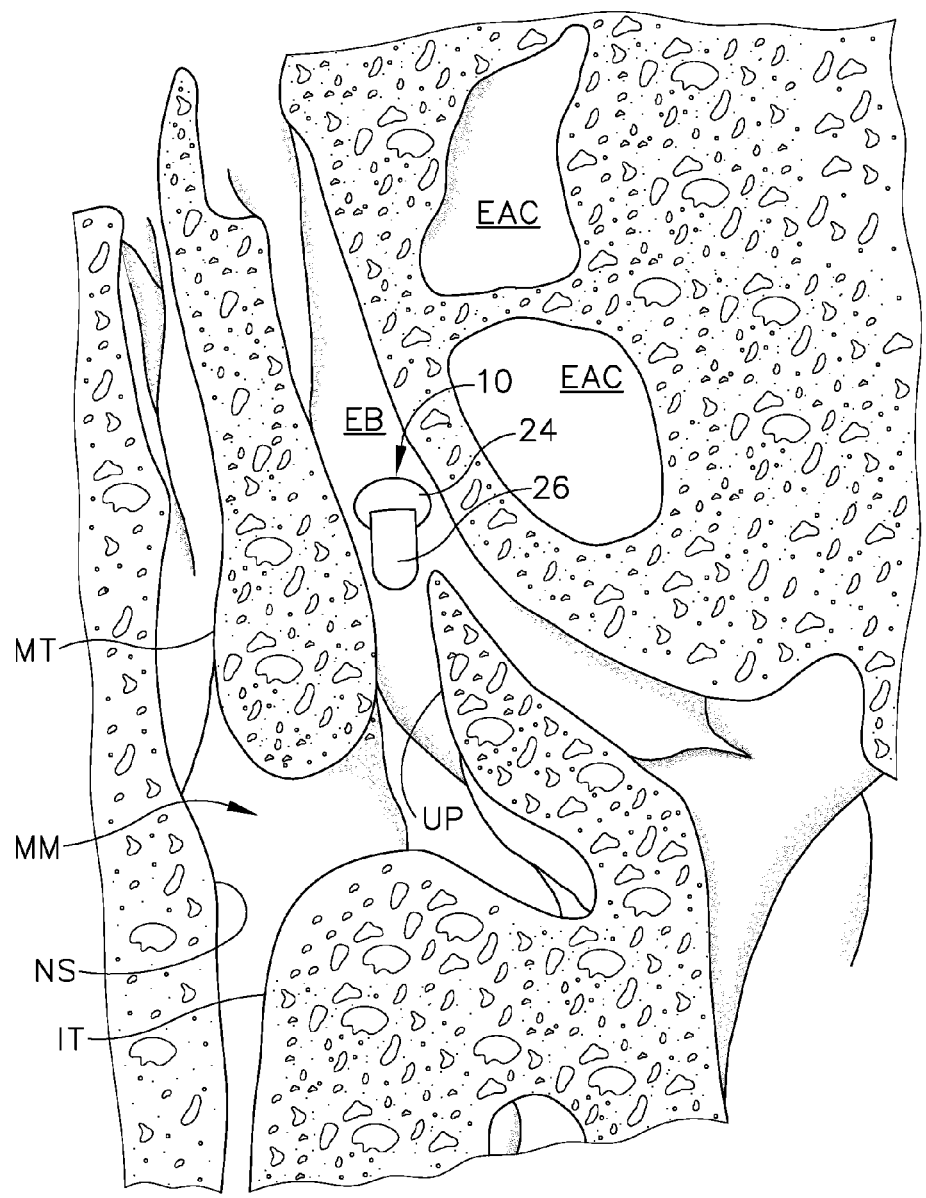
FIG. 5 depicts an enlarged anterior coronal cross-sectional view of a portion of a human head, showing the implant of FIG. 4 positioned in the ethmoid bulla.

FIGS. 1-3 show views of various sinus structures in a portion of a human head. In particular, FIG. 1 shows a left sagittal cross-sectional view of a portion of a human head. FIG. 2 shows a coronal cross-sectional view of the human head, looking posteriorly from an anterior perspective. FIG. 3 shows an axial cross-sectional view of the human head, looking inferiorly from a superior perspective. As best seen in FIG. 1, the human head includes a sphenoid sinus (SS), ethmoid sinus (ES), frontal sinus (FS), middle turbinate (MT), middle turbinate horizontal basal lamella (MThBL), middle turbinate vertical basal lamella (MTvBL), inferior turbinate (IT), uncinate process (UP), and lateral nasal wall (LNW). As best seen in FIG. 2, the human head also includes a frontal recess (FR), an ethmoid infundibulum (EI), a maxillary sinus (MS), a middle meatus (MM), and a nasal septum (NS). The frontal recess (FR) is inferior to the frontal sinus (FS). The ethmoid infundibulum (EI) is defined by the ethmoid bulla (EB) and the uncinate process (UP). The ethmoid infundibulum (EI) leads to the maxillary sinus (MS). The middle meatus (MM) is a passageway defined as the space lateral to the middle turbinate (MT).

The ethmoid sinus (ES) comprises a set of sinus cells (EAC) that may be categorized as anterior ethmoid sinus (AES) cells and posterior ethmoid sinus (PES) cells. The ethmoid bulla (EB), which is the primary anterior ethmoid air cell (EAC), is generally inferior and anterior to the other anterior ethmoid sinus (AES) cells (EACs) and posterior ethmoid sinus (PES) cells (EACs). The posterior wall of the ethmoid bulla (EB) and the middle turbinate vertical basal lamella (MTvBL) together define a retrobullar space (RBS). It should be understood that anatomical variation in the human is such that this retrobullar space (RBS) may or may not be present in a given individual.

The ethmoid sinus (ES) includes ostia (not shown) for providing fluid communication to and from the cells of the ethmoid sinus (ES) and the nasal cavity. For instance, ostia may provide fluid paths for cells (EACs) within the anterior ethmoid sinus (AES), cells (EACs) within the posterior ethmoid sinus (PES), and the ethmoid bulla (EB). In some instances, suprabullar cells (EACs) of the ethmoid sinus (ES) drain into the ethmoid bulla (EB) cell (EAC). Some suprabullar cells (EACs) may drain directly into the retrobullar space (RBS). The ethmoid bulla (EB) may itself provide fluid communication with the nasal cavity via one or more ostia, such that the ethmoid bulla (EB) may provide a fluid communication path between the other ethmoid sinus (ES) cells (EACs) (that drain into the ethmoid bulla (EB) cell (EAC)) and the nasal cavity. For instance, the ethmoid bulla (EB) may provide fluid communication through an ostium at the retrobullar space (RBS). The fluid communication paths provided by ostia may allow the entry of air and liquids (e.g., medications); while also allowing drainage of mucus. In some instances, the ostia may become blocked, may become functionally closed due to mucosal thickening, or may otherwise not provide sufficient fluid communication. In addition or in the alternative, the configuration of the retrobullar space (RBS) may impede flow through the ostium of the ethmoid bulla (EB).

The following examples of fluid delivery implants and port implants are described mainly in the context of the ethmoid bulla (EB). However, it should be understood that this context is merely illustrative, and that the below teachings are not limited to the ethmoid bulla (EB) sinus wall. The various fluid delivery implants and port implants described below may alternatively be implanted in other sinus walls, as will be apparent to those of ordinary skill in the art in view of the teachings herein.

II. EXEMPLARY FLUID DELIVERY IMPLANTS FOR SINUS WALLS

In some clinical contexts, it may be desirable to deploy a wick or other type of fluid delivery implant in the ethmoid bulla (EB) and/or in other sinus cavities. A fluid delivery implant may promote communication of medical fluids to the mucosa of the ethmoid bulla (EB) through a capillary action. This capillary action may be enhanced by maximizing contact between the wick material and the mucosa in the ethmoid bulla (EB) or other sinus cavity. At least part of the fluid delivery implant may be bioabsorbable and may itself be formed in part by a therapeutic material. The degree to which material used in the implant is hydrophilic or hydrophobic may be manipulated to provide a desired type of fluid transport. By way of example only, fluids that may be communicated by a fluid delivery implant may include saline, a combination of saline and a surfactant, an anti-inflammatory (e.g., mometasone, etc.), an antibiotic, an anti-fungal, anti-microbial, surfactants, and/or various other kinds of fluids/medications, including combinations thereof. Various examples of intrasinus and intersinus fluid delivery implants will be described in greater detail below, while other examples will be apparent to those of ordinary skill in the art in view of the teachings herein. Similarly, various kinds of fluids that may be delivered using the implants described below will be apparent to those of ordinary skill in the art in view of the teachings herein.

It should be understood that the various fluid delivery implants described below may be deployed in a naturally occurring ostium, in an enlarged natural ostium, and/or in a created ostium. By way of example only, the fluid delivery implants described herein may be deployed in a naturally occurring ostium that has been enlarged in accordance with at least some of the teachings of U.S. Pub. No. 2011/0004057, now abandoned, the disclosure of which is incorporated by reference herein. As another merely illustrative example, the fluid delivery implants described herein may be deployed in an ostium that has been created in accordance with at least some of the teachings of U.S. patent application Ser. No. 14/038,867, entitled "Apparatus and Method for Treatment of Ethmoid Sinusitis," filed on Sep. 27, 2013 published as U.S. Pat. Pub. No. 2014/0277039 on Sep. 18, 2014, now abandoned, the disclosure of which is incorporated by reference herein. Furthermore, the fluid delivery implants described herein may be deployed in an ostium that has been first created in accordance with at least some of the teachings of U.S. patent application Ser. No. 14/038,867, entitled "Apparatus and Method for Treatment of Ethmoid Sinusitis," filed on Sep. 27, 2013, published as U.S. Pat. Pub. No. 2014/0277039 on Sep. 18, 2014, now abandoned, the disclosure of which is incorporated by reference herein; then enlarged in accordance with at least some of the teachings of U.S. Pub. No. 2011/0004057, now abandoned, the disclosure of which is incorporated by reference herein. Other settings in which the below described fluid delivery implants may be deployed will be apparent to those of ordinary skill in the art in view of the teachings herein.

A. Exemplary Sinus Wall Implant with Paddle

FIGS. 4-6B show an exemplary fluid delivery implant (10) positioned in an ethmoid bulla (EB). Implant (10) of this example comprises a retainer body (12), a first flange (14), a second flange (16), a foam member (20), a brace (22), a compression member (24), and a paddle (26). In the present example, body (12) is substantially cylindraceous, while flanges (14, 16) and compression member (24) are disc-shaped. Alternatively, any other suitable configurations may be used. Body (12) defines a passageway (30) extending through the full length of body (12). While a single large passageway (30) is shown, it should be understood that body (12) may instead define several smaller passageways. Body (12) is configured to fit in an opening of the ethmoid bulla (EB), with flanges (14, 16) cooperating to retain body (12) in the opening like a grommet. In the present example, flange (14) is flexible enough to enable flange (14) to pass through the opening without widening the opening; yet rigid enough to substantially maintain the position of body (12) in the opening. Various suitable materials and configurations that may be used to form flange (14) will be apparent to those of ordinary skill in the art in view of the teachings herein. Furthermore, various suitable ways in which body (12) may be inserted into the opening in the ethmoid bulla (EB) will be apparent to those of ordinary skill in the art in view of the teachings herein.

Figure 6A:
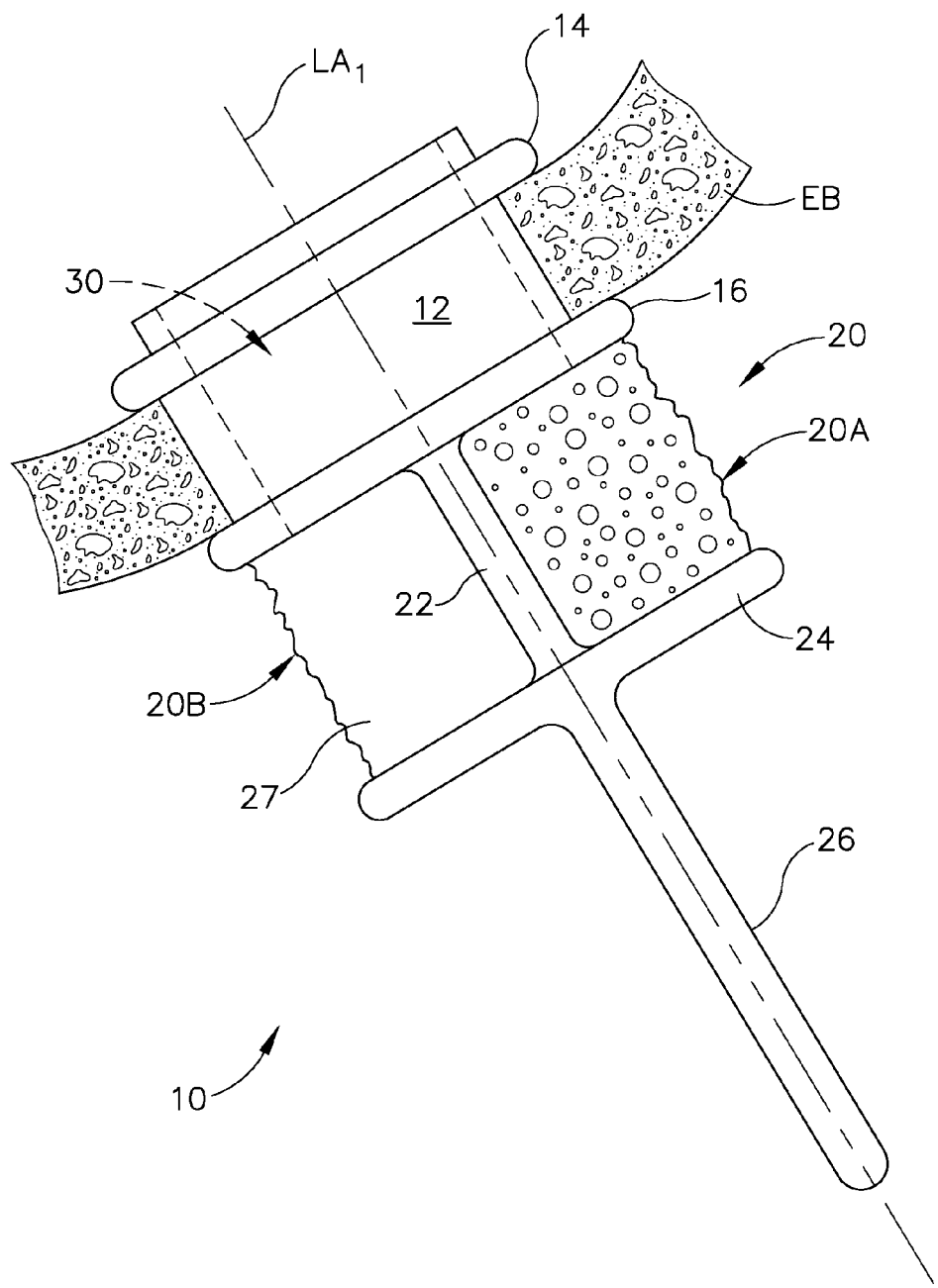
FIG. 6A depicts a side elevational view of the implant of FIG. 4, with a portion of the ethmoid bulla in cross-section, and with the implant in a relaxed state.

Foam member (20) comprises an open cell material that is configured to hold a fluid such as any of the various fluids referred to herein and/or any other suitable fluid as will be apparent to those of ordinary skill in the art in view of the teachings herein. Passageway (30) of body (12) is in fluid communication with foam member (20). Brace (22) extends through foam member (20) and couples compression member (24) with flange (16). Brace (22) divides foam member (20) into an anterior portion (20a) and a posterior portion (20b). In the present example, posterior portion (20b) is covered with a fluid impermeable skin (27), while anterior portion (20a) lacks a skin such that the open cells of anterior portion (20a) are exposed. Brace (22) is flexible and includes several fenestrations (not shown) formed therethrough, allowing fluid to be transferred within foam member (20) across brace (22). Paddle (26) projects from compression member (24). In some variations, brace (22) is substantially rigid but is joined with flange (16) by a living hinge or other flexible feature. Paddle (26) and compression member (24) are both substantially rigid. Brace (22) is resiliently biased to assume a substantially straight configuration, whereby body (12), flanges (14, 16), brace (22), compression member (24), and paddle (26) are aligned along a longitudinal axis ($LA_1$) as shown in FIG. 6A.

Figure 6B:
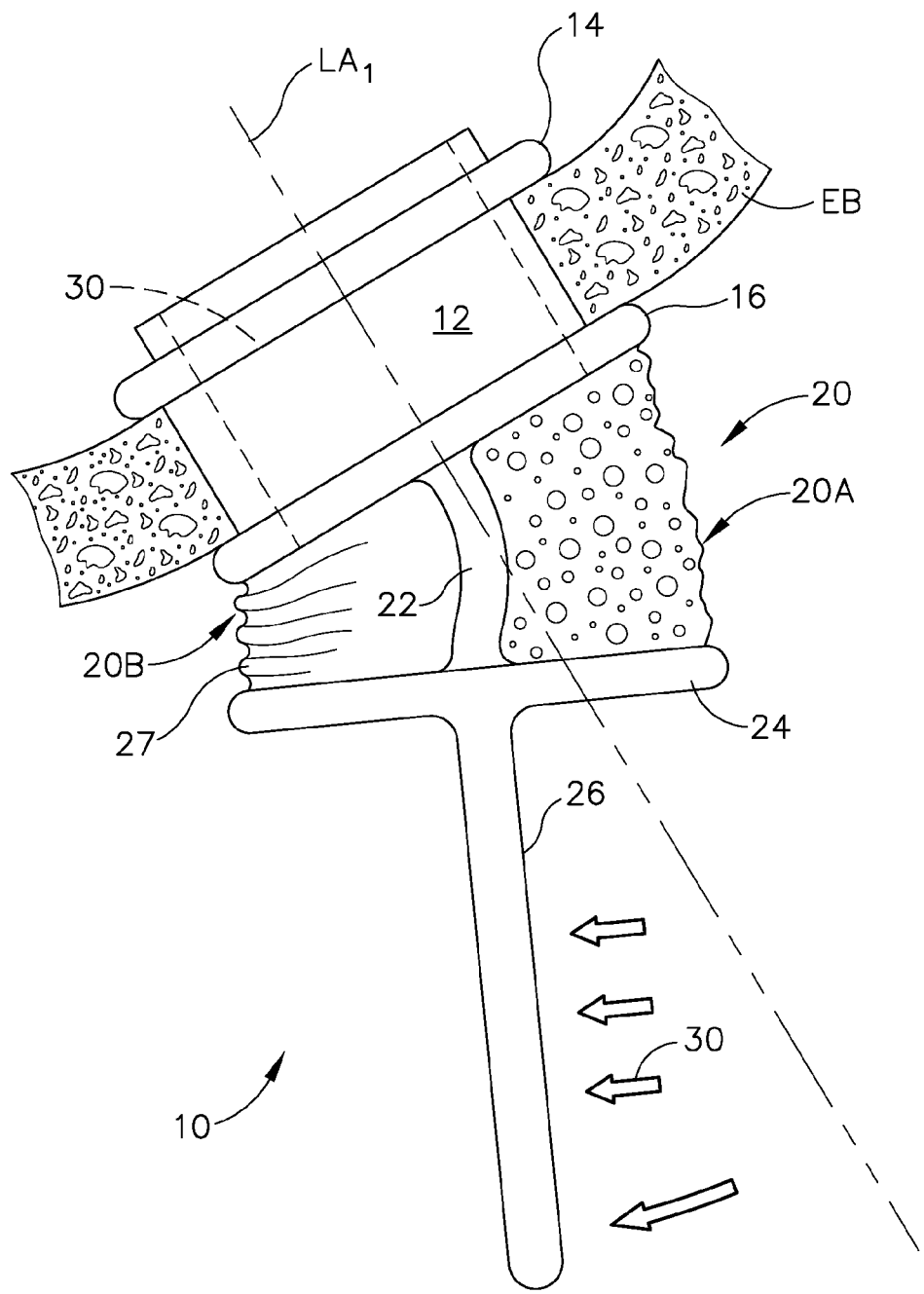
FIG. 6B depicts a side elevational view of the implant of FIG. 4, with a portion of the ethmoid bulla in cross-section, and with the implant in an actuated state.
Figure 7:
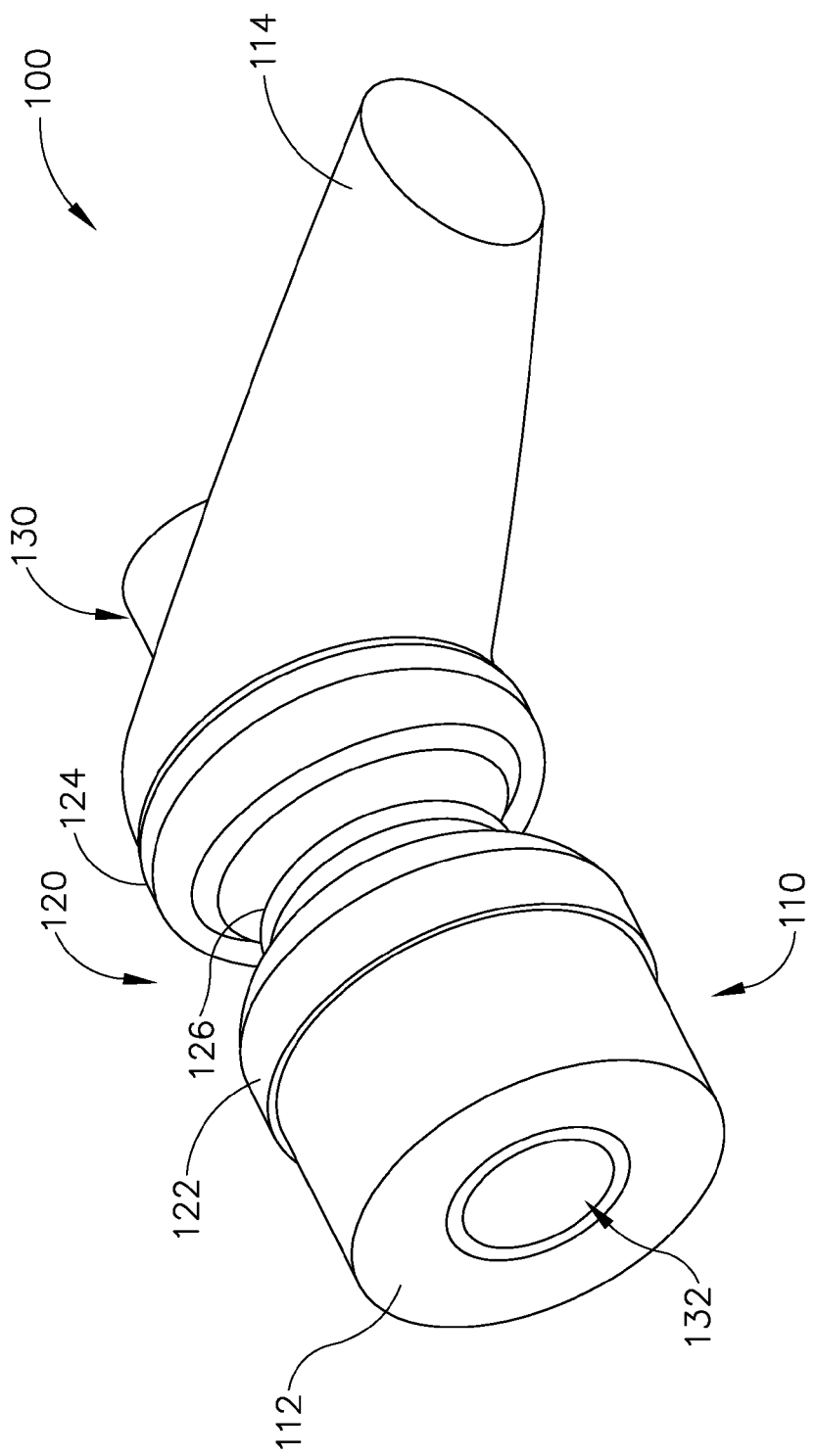
FIG. 7 depicts a perspective view of another exemplary sinus implant.
Figure 8:
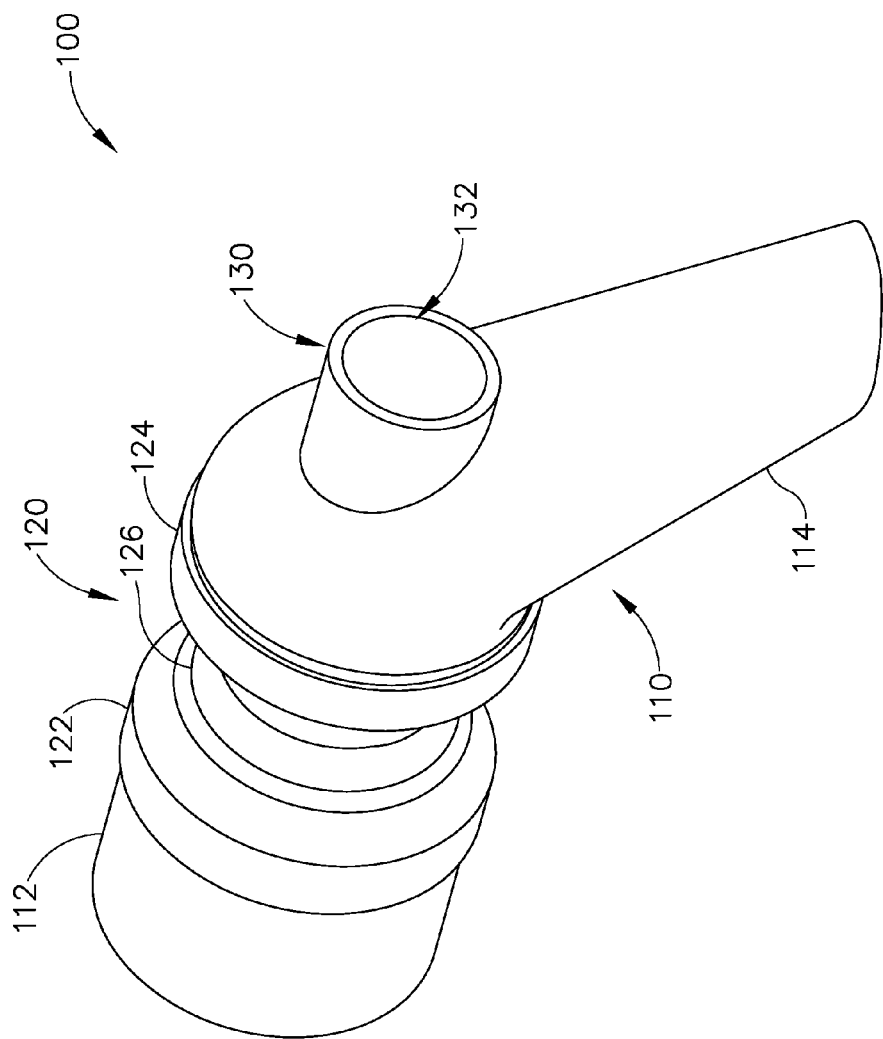
FIG. 8 depicts another perspective view of the implant of FIG. 7.
Figure 9:
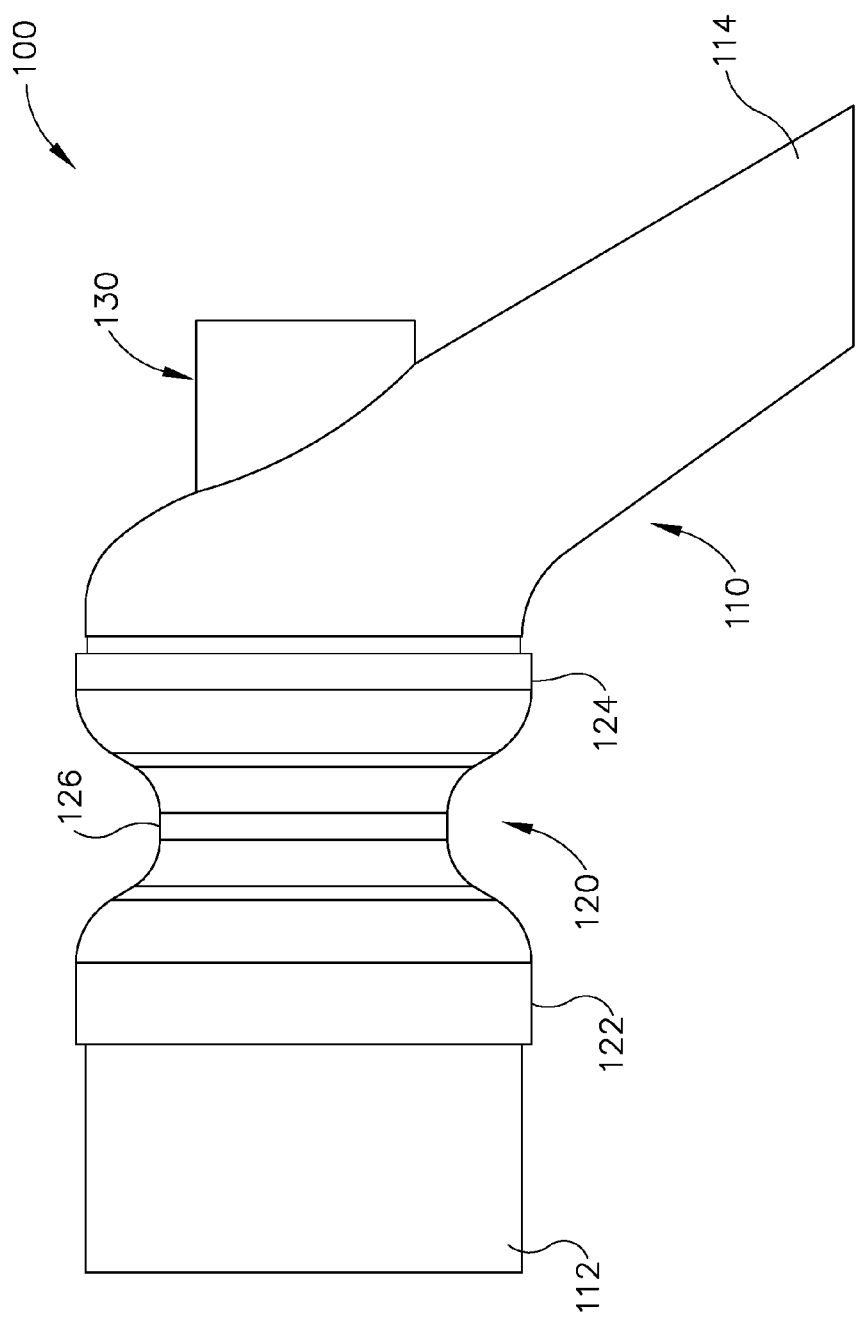
FIG. 9 depicts a side elevational view of the implant of FIG. 7.

Implant (10) is implanted at an orientation where inspired air (30) will impose against paddle (26), as shown in FIG. 6B. In particular, paddle (26) presents a broad face that is normal to the main vector of inspiratory air flow, such that inspired air (30) urges paddle (26) posteriorly, deflecting paddle (26) away from the longitudinal axis (LA$_1$), which causes brace (22) to flex. As brace (22) flexes, compression member (24) compresses a posterior region of foam member (20) against flange (16). This compression of foam member (20) urges fluid out of foam member (20) and through passageway (30) into the cell (EAC) of the ethmoid bulla (EB). Such transport of fluid is provided because posterior portion (20b) is covered in impermeable skin (27) and because posterior portion (20b) is compressed while anterior portion (20a) is expanded.

In some versions, expired air urges paddle (26) anteriorly, deflecting paddle (26) away from the longitudinal axis (LA$_1$) in the direction opposite to that shown in FIG. 6B. This may cause compression member (24) to compress an anterior region of foam member (20) against flange (16). This compression of foam member (20) may also urge fluid out of foam member (20). In some other versions, expired air simply urges paddle (26) back to the position shown in FIG. 6A.

In some variations, foam member (20) is substituted or supplemented with a pump feature that is actuated by deflection of paddle (26) away from the longitudinal axis (LA$_1$). For instance, repeated deflection of paddle (26) may drive a ratcheting feature that progressively compresses a bellows reservoir, a diaphragm pump, and/or some other kind of pumping feature. Various suitable kinds of pumping features that may be driven by paddle (26) will be apparent to those of ordinary skill in the art in view of the teachings herein.

It should be understood that implant (10) may be implanted with or without fluid already in foam member (20). Regardless, the physician or patient may add fluid to foam member (20) after implantation using any suitable known nasal fluid administration device or technique (e.g., aerosolized spray, non-aerosolized flush, etc.). Fluids delivered in such a fashion may readily reach foam member (20) and thereby be absorbed by foam member (20) via anterior portion (20a). In some such instances, foam member (20) may need to be replenished with fluid on a periodic basis.

B. Exemplary Sinus Wall Implant with Port and Wicking Feature

Figure 10:
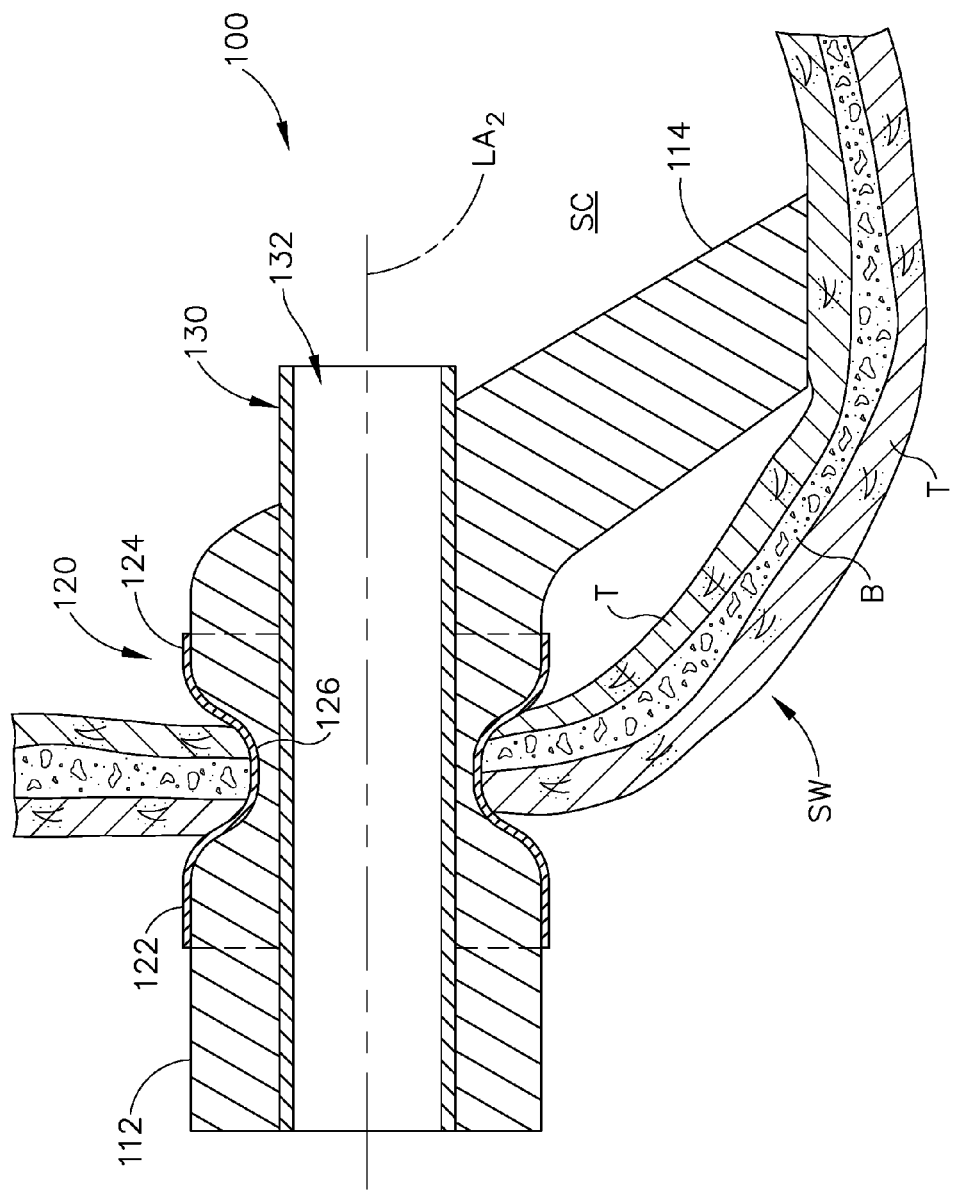
FIG. 10 depicts a cross-sectional view of the implant of FIG. 7 positioned in a sinus wall.

FIGS. 7-10 show another exemplary implant (100) that may be implanted in a sinus wall (SW). Sinus wall (SW) comprises a thin layer of bone (B) interposed between two layers of tissue (T). To the extent that other depictions of sinus walls in the present drawings do not include depictions of tissue layers, it should be understood that those sinus walls may still in fact include tissue layers surrounding a layer of bone just as depicted in FIG. 10. Implant (100) of this example comprises a porous foam body (110), a non-permeable feature (120), and a port tube (130). Foam body (110) comprises a proximal portion (112) and a distal wick feature (114). Port tube (130) defines a lumen (132). Non-permeable feature (120) and port tube (130) are coaxially aligned with each other along a common longitudinal axis (LA$_2$), while wick feature (114) extends obliquely relative to longitudinal axis (LA$_2$).

In the present example, foam body (110) is formed of polyvinyl alcohol (PVA) foam. Alternatively, any other suitable materials or combinations of materials may be used. It should also be understood that pores may be formed in foam body (110) using a variety of techniques. By way of example only, pores may be formed through the use of sacrificial material that is dissolved or otherwise removed following the forming of the material of body (110). As another merely illustrative example, pores may be formed by infusing gas into the material of body (110) as it is formed, or by including chemical components that combine in a gas-forming reaction as the material of body (110) is formed. Other suitable ways in which pores may be formed will be apparent to those of ordinary skill in the art in view of the teachings herein. It should also be understood that body (110) may include capillaries and/or microcapillaries.

Body (110) and non-permeable feature (120) are configured to fit in an opening of a sinus wall (SW) (e.g., the antero-inferior wall of the ethmoid bulla (EB)). FIGS. 7-10 show non-permeable feature (120) as defining an enlarged proximal region (122), an enlarged distal region (124), and a recess (126) positioned longitudinally between regions (122, 124). In some versions, non-permeable feature (120) is preformed to have this configuration, such that enlarged regions (122, 124) cooperate to retain body (110) and non-permeable feature (120) in the opening. Non-permeable feature (120) may thus be configured as a resilient grommet. In the present example, non-permeable feature (120) is flexible enough to enable non-permeable feature (120) to pass through the opening without widening the opening; yet rigid enough to substantially maintain the position of body (110) and non-permeable feature (120) in the opening.

In some other versions, non-permeable feature (120), is fully compliant, has a generally cylindraceous preformed configuration, or has some other preformed configuration; and non-permeable feature (120) assumes the configuration shown in FIGS. 7-10 after implant (100) is positioned in an opening formed in a sinus wall (SW). In other words, the edge of the sinus wall (SW) that defines the opening in which implant is inserted (100) may cause non-permeable feature (120) to deform to assume the shape shown in FIGS. 7-10. As another merely illustrative example, non-permeable feature (120) may simply comprise a fully compliant sleeve, such that an outward resilient bias of body (110) effectively creates enlarged regions (122, 124) when implant (100) is positioned in an opening of a sinus wall (SW) that has a diameter smaller than an expanded diameter of body (110). A relatively smaller diameter of an opening formed in the sinus wall (SW) may thus deform non-permeable feature (120) and body (110) to the configuration shown in FIGS. 7-10, such that an outward bias of body (110) creates friction to hold implant (100) in place in the sinus wall (SW). In addition or in the alternative, distal wick feature (114) may provide retention of body (110) relative to the sinus wall (SW). Other suitable ways in which implant (100) may be retained in the sinus wall (SW) will be apparent to those of ordinary skill in the art in view of the teachings herein. Furthermore, various suitable ways in which body (110), non-permeable feature (120), and distal wick feature (114) may be inserted into the opening in the sinus wall (SW) will be apparent to those of ordinary skill in the art in view of the teachings herein.

It should be understood that non-permeable feature (120) is formed of a material that is fluid impermeable, such that fluid does not pass from body (110) to the sinus wall (SW) at (or immediately adjacent to) the opening formed in the sinus wall (SW). Various suitable materials and configurations that may be used to form non-permeable feature (120) will be apparent to those of ordinary skill in the art in view of the teachings herein. By way of example only, non-permeable feature (120) may comprise a non-permeable sleeve disposed about body (110), a non-permeable skin or film deposited on body (110), a non-permeable coating provided on body (110), a region of body (110) where pores are closed or filled to render that region of body (110) impermeable by fluid, etc. In some variations, body (110)

includes additional non-permeable features that prevent the communication of fluid out of body (110) along certain regions of the length of body (110). Such additional non-permeable features may be positioned distal to and/or proximal to non-permeable feature (120). Even when additional non-permeable features are included, the distal end of wicking feature (114) remains exposed such that body (110) may emit fluid at the distal end of wicking feature (114). Other suitable ways in which non-permeable feature (120) may be formed will be apparent to those of ordinary skill in the art in view of the teachings herein.

As shown in FIG. 10, implant (100) is implanted such that the sinus wall (SW) is positioned in recess (126) of non-permeable feature (120) and such that wick feature (114) is in contact with a layer of mucosal tissue (T) in the sinus cavity (SC). The oblique orientation of wick feature (114) may promote contact between wick feature (114) and the mucosal tissue (T), reducing chances of wick feature (114) being impeded by internal partitions within the sinus cavity (SC). It should be understood that contact between wick feature (114) and the mucosal tissue (T) of sinus cavity (SC) may promote a capillary action through body (110) such that fluid reaching proximal end (112) of body (110) is wicked through body (110), thereby reaching the mucosal tissue (T) of sinus cavity (SC) via wick feature (114). It should also be understood that the non-permeability of non-permeable feature (120) will prevent the fluid from being communicated directly to tissue (T) at (or adjacent to) the opening formed in the sinus wall (SW). Non-permeable feature (120) thus prevents the formation of a fluid short circuit between tissue (T) and body (110) upstream of wick feature (114). Proximal end (112) of body (110) is positioned exterior to the sinus wall (SW) and sinus cavity (SC). Proximal end (112) of body (110) is thus exposed within the nasal cavity, such that proximal end (112) may receive fluid by a physician or the patient using any suitable known nasal fluid administration device or technique (e.g., aerosolized spray, non-aerosolized flush, etc.). The physician or patient may administer fluid to body (110) to at least a point where body (110) becomes fully saturated. In some instances, the physician or patient continues to deliver fluid to body (110) after body (110) has become saturated, to further ensure further delivery of the fluid to the mucosal tissue (T) of sinus cavity (SC) via wick feature (114).

Port tube (130) may be formed of a bioresorbable material or a non-bioresorbable material. By way of example only, port tube (130) may comprise polydimethylsiloxane, polyurethane, polydiaxanone, polylactic acid, polyglycolic acid, other biocompatible materials, or combinations thereof. Lumen (132) of port tube (130) is configured to provide ventilation of sinus cavity (SC) and to provide a pathway for drainage of fluid (e.g., excess mucus) from sinus cavity (SC). It should therefore be understood that implant (100) of this example provides a combination of fluid delivery (through wicking feature (114)), ventilation (through lumen (132)), and drainage (through lumen (132)) for a sinus cavity (SC). It should also be understood that drainage via lumen (132) may be encouraged by gravity (e.g., when the patient is lying down) and/or mucociliary transport.

Figure 11:
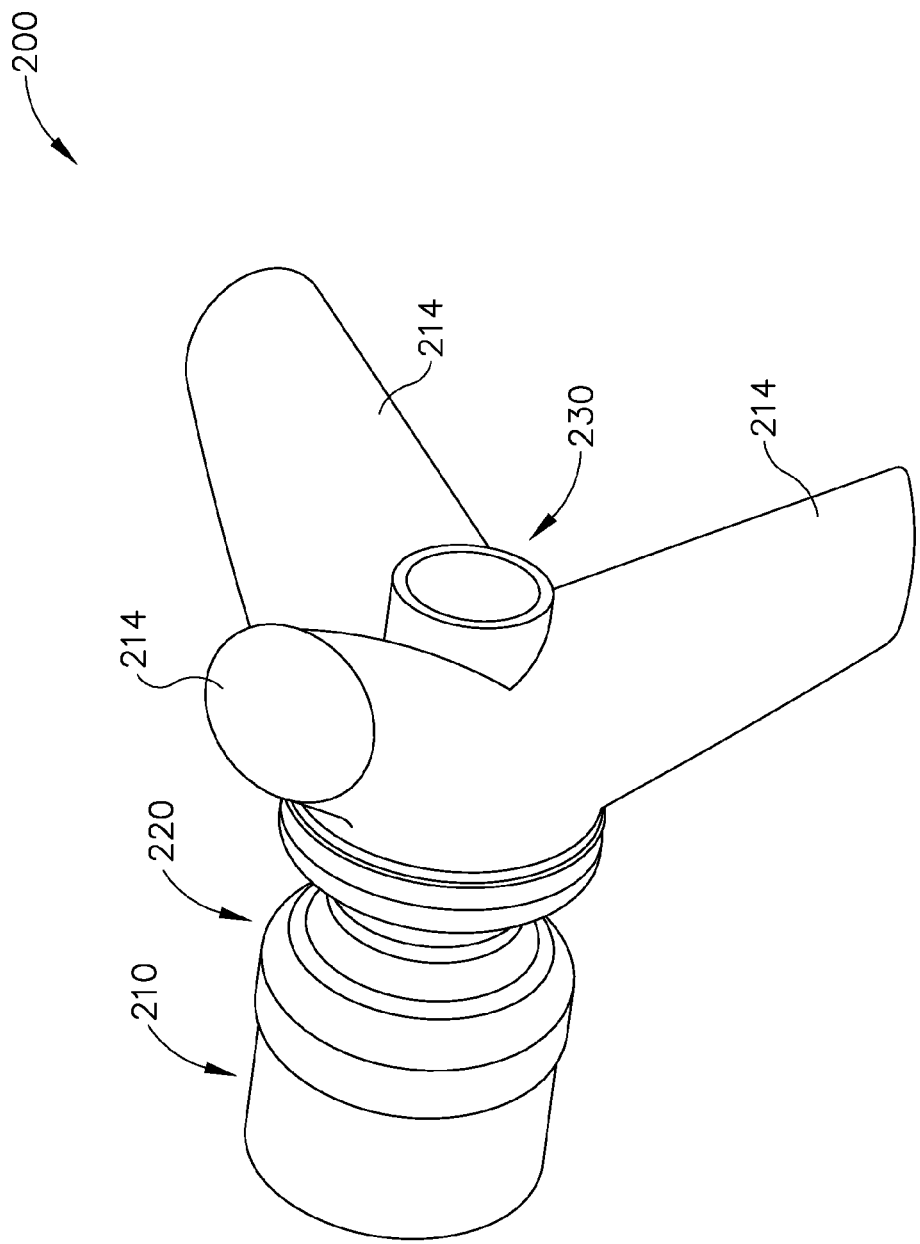
FIG. 11 depicts a perspective view of another exemplary sinus implant.
Figure 12:
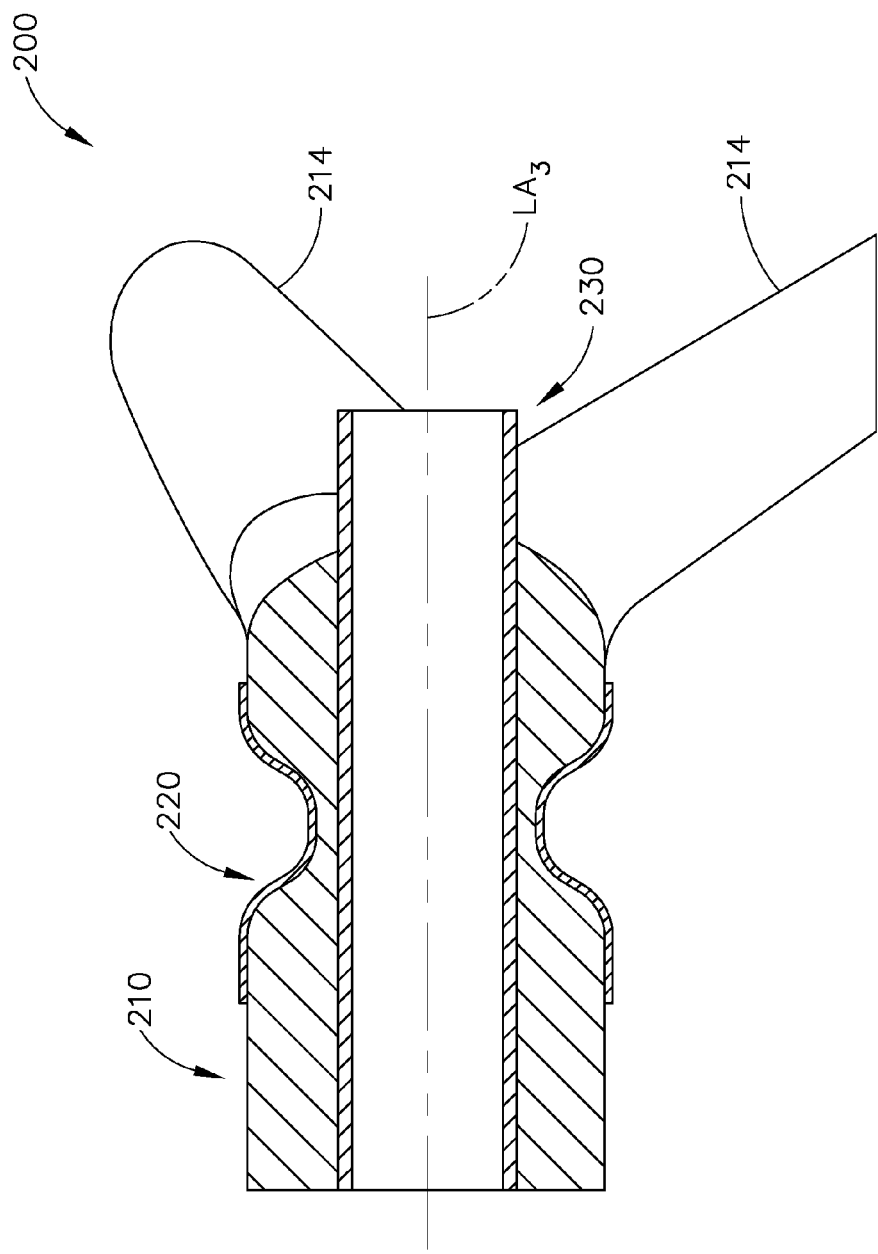
FIG. 12 depicts a cross-sectional view of the implant of FIG. 11.

FIGS. 11-12 show an exemplary variation of implant (100). In particular, FIGS. 11-12 show an exemplary implant (200) that comprises a porous foam body (210), an outer non-permeable feature (220), and a port tube (230). Non-permeable feature (220) and port tube (230) are substantially identical to non-permeable feature (120) and port tube (130) described above. Body (210) is substantially similar to body (110) described above, except that body (210) of this example include three wick features (214). Wick features (214) all extend obliquely relative to a longitudinal axis (LA₃) shared by non-permeable feature (120) and port tube (130). Wick features (214) are also equidistantly spaced about longitudinal axis (LA₃). It should be understood that having a plurality of wick features (214) may further enhance the communication of fluid from body (210) to the mucosal tissue (T) of sinus cavity (SC) by providing additional routes for capillary action. It should also be understood that any other suitable number of wick features (214) may be provided. Still other suitable variations of implants (100, 200) will be apparent to those of ordinary skill in the art in view of the teachings herein.

C. Exemplary Sinus Wall Implant with Dendrites

Figure 13:
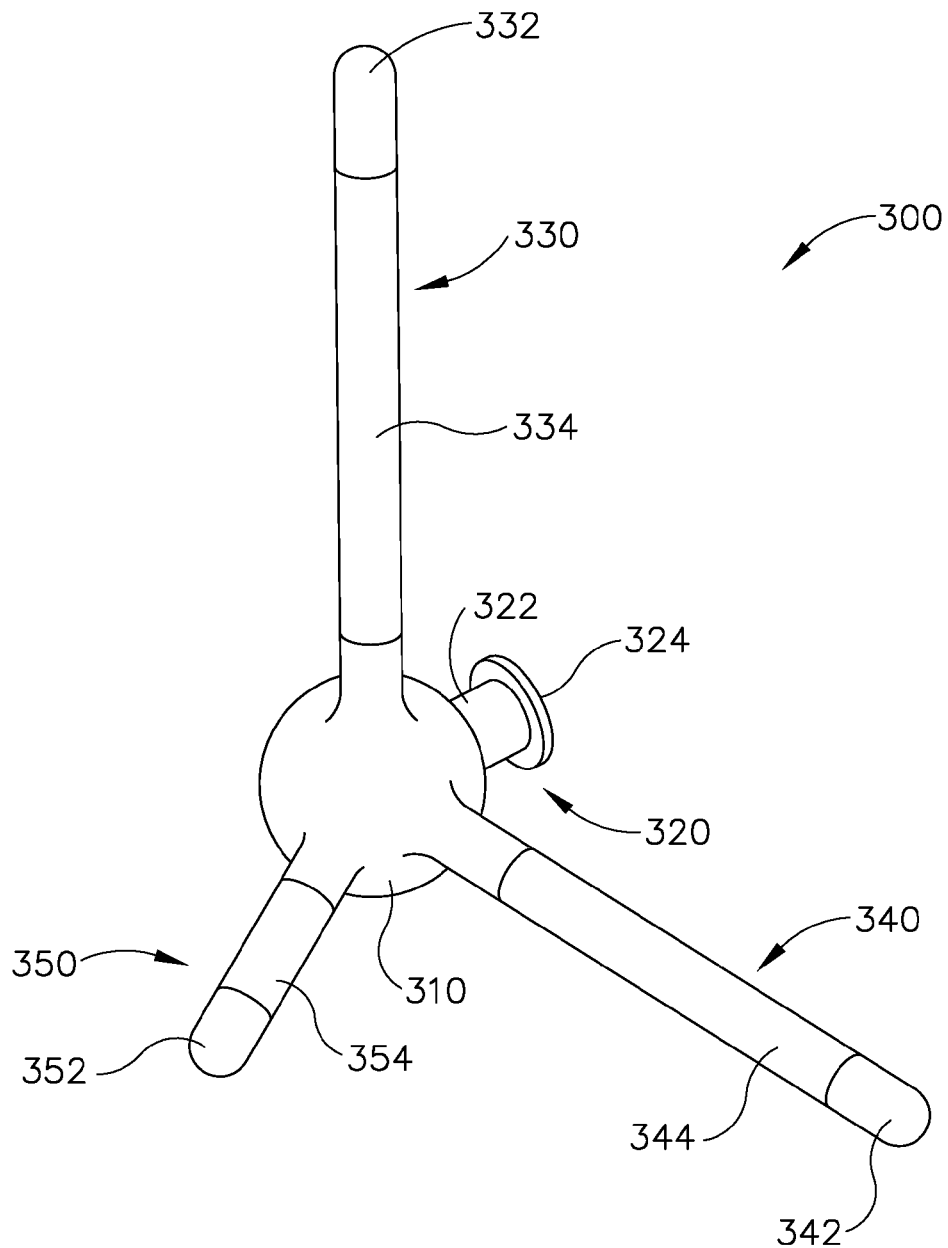
FIG. 13 depicts a perspective view of another exemplary sinus implant.
Figure 14:
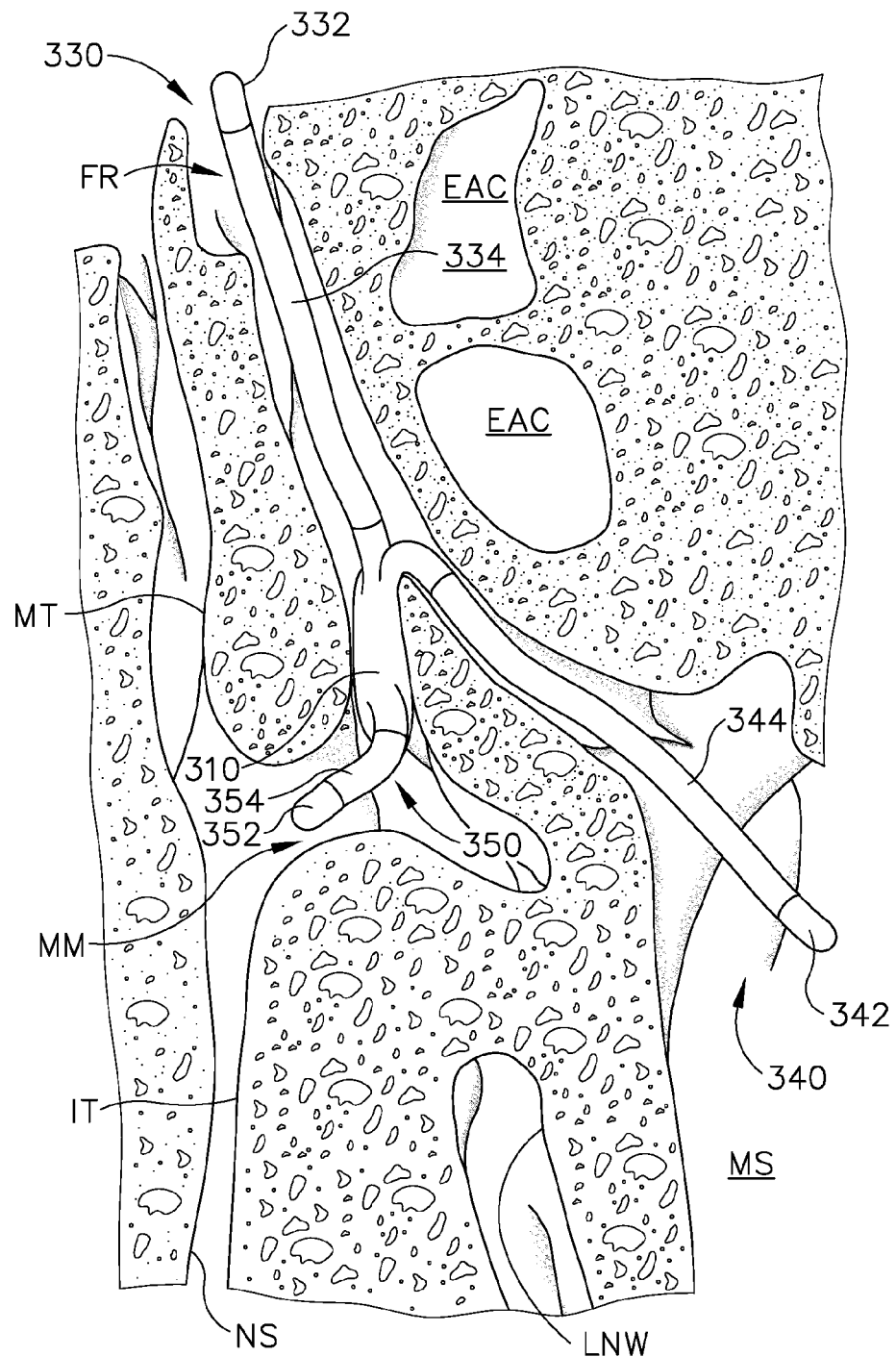
FIG. 14 depicts an enlarged anterior coronal cross-sectional view of a portion of a human head, showing the implant of FIG. 13 positioned in the middle meatus with dendrites extending into the frontal recess, the maxillary sinus, and the anterior middle meatus.
Figure 15:
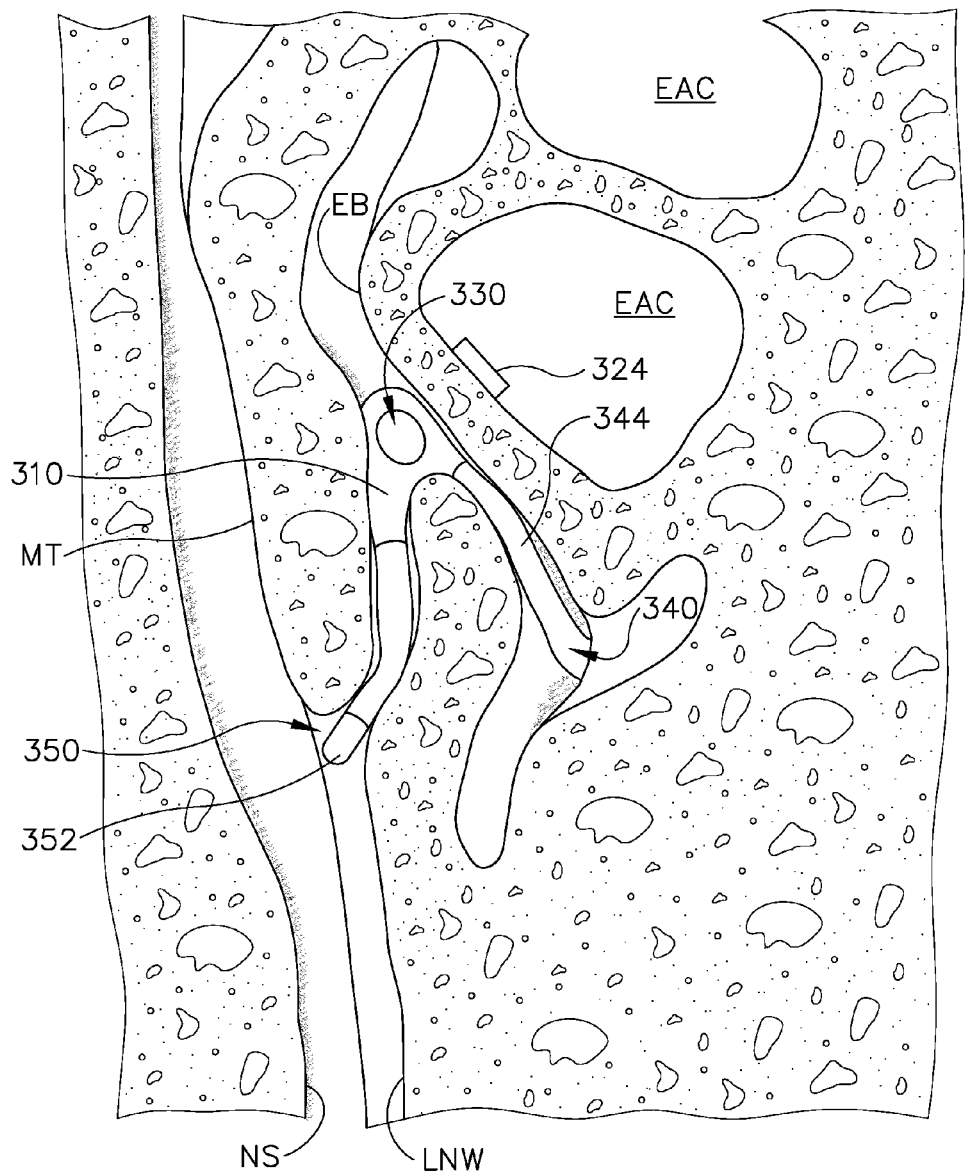
FIG. 15 depicts an enlarged superior axial cross-sectional view of a portion of a human head, showing the implant of FIG. 13 positioned in the middle meatus with dendrites extending into the frontal recess, the maxillary sinus, and the anterior middle meatus, with an anchor member positioned in the ethmoid bulla.

FIGS. 13-15 show an exemplary implant (300) that comprises a porous foam body (310), an anchor feature (320), a first dendrite (330), a second dendrite (340), and a third dendrite (350). Anchor feature (320) includes a body (322) and a retention flange (324). Body (322) is configured to fit in an opening of the ethmoid bulla (EB), with flange (324) being configured to retain body (322) in the opening. Body (322) includes a non-permeable material such that fluid does not leak through the exterior of body. In the present example, flange (324) is flexible enough to enable flange (324) to pass through the opening without widening the opening; yet rigid enough to substantially maintain the position of body (322) in the opening. Various suitable materials and configurations that may be used to form (324) will be apparent to those of ordinary skill in the art in view of the teachings herein. Furthermore, various suitable ways in which body (324) may be inserted into the opening in the ethmoid bulla (EB) will be apparent to those of ordinary skill in the art in view of the teachings herein.

Body (310) and dendrites (330, 340, 350) are formed of an open cellular porous material, such as polyvinyl alcohol (PVA) foam. Each dendrite (330, 340, 350) includes a respective free end (332, 342, 352) and a non-permeable skin (334, 344, 354) extending along part of the length of dendrite (330, 340, 350). When body (310) and dendrites (330, 340, 350) are saturated with fluid, skin (334, 344, 354) prevents dendrites (330, 340, 350) from emitting the fluid along the regions that are covered by skins (334, 344, 354). However, free ends (332, 342, 352) are exposed relative to skins (334, 344, 354), such that dendrites (330, 340, 350) are able to emit fluid at free ends (332, 342, 352). Body (310) is also exposed relative to skins (334, 344, 354), such that body (310) is capable of absorbing incident fluids. In particular, body (310) serves as a fluid hub in the present example, with fluid that is absorbed at body (310) being delivered to tissue through free ends (332, 342, 352) of dendrites (330, 340, 350).

In an exemplary use, body (310) is implanted in the middle meatus (MM), as shown in FIGS. 14-15. Anchor feature (320) is secured to the ethmoid bulla (EB). First dendrite (330) is positioned such that free end (332) is located in the frontal recess (FR), contacting tissue therein. Second dendrite (340) is routed through the ethmoid infundibulum (EI) and maxillary ostium such that free end (342) is located in the maxillary sinus (MS), contacting tissue therein. Third dendrite (350) is positioned such that free end (352) is located in the anterior middle meatus (MM). It should be understood that dendrites (330, 340, 360) may be positioned in any suitable order using any suitable instruments and techniques. It should also be understood that anchor feature (320) may be secured to the ethmoid bulla (EB) before or after any or all of dendrites (330, 340, 360) are positioned. Moreover, implant (300) may be anchored in place in some other fashion.

Once implant (300) is positioned, the physician or patient may administer fluid within the nasal cavity using any suitable known nasal fluid administration device or technique (e.g., aerosolized spray, non-aerosolized flush, etc.). The fluid will eventually reach body (310) which will absorb the fluid. As body (310) becomes saturated, the fluid will wick through dendrites (330, 340, 360) and reach the frontal recess (FR), maxillary sinus (MS), and anterior middle meatus (MM) through capillary action as described above. When saturated, free ends (332, 342, 352) may expand to increase surface area contact with adjacent mucosal tissue. In some instances, dendrite (350) serves as a fluid input for implant (300), such that fluid introduced to the nasal cavity is first incident on free end (352), where it is drawn in and eventually wicked through body (310) and the other dendrites (340, 350) to reach the frontal recess (FR) and maxillary sinus (MS). Thus, in some alternative versions, body (310) is covered with a skin such that free ends (332, 342, 352) are the only portions of the porous material that are exposed. Still other variations of implant (300) will be apparent to those of ordinary skill in the art in view of the teachings herein.

III. EXEMPLARY REMOVABLE PORT IMPLANT FOR SINUS WALL

As noted above, naturally occurring and/or surgically formed ostia may provide a path for fluid communication between a sinus cavity and the nasal cavity, allowing air and liquids (e.g., medications, etc.) to enter the sinus cavity; and mucus to exit the sinus cavity. In some instances, the ostia may become blocked, may become functionally closed due to mucosal thickening, or may otherwise not provide sufficient fluid communication. A port may be implanted in order to maintain patency through an ostium. Some examples of sinus ostium ports are described above. Additional examples of sinus ostium ports are described in U.S. patent application Ser. No. 14/038,867, entitled "Apparatus and Method for Treatment of Ethmoid Sinusitis," filed on Sep. 27, 2013, published as U.S. Pat. Pub. No. 2014/0277039 on Sep. 18, 2014, now abandoned, the disclosure of which is incorporated by reference herein. In some instances, it may be desirable to provide one or more features that enable a sinus ostium port to the removed from the patient with relative ease, without imposing trauma on the sinus wall or adjacent structures. One merely illustrative example of such a port feature will be described in greater detail below, while other examples will be apparent to those of ordinary skill in the art in view of the teachings herein.

Figure 16:
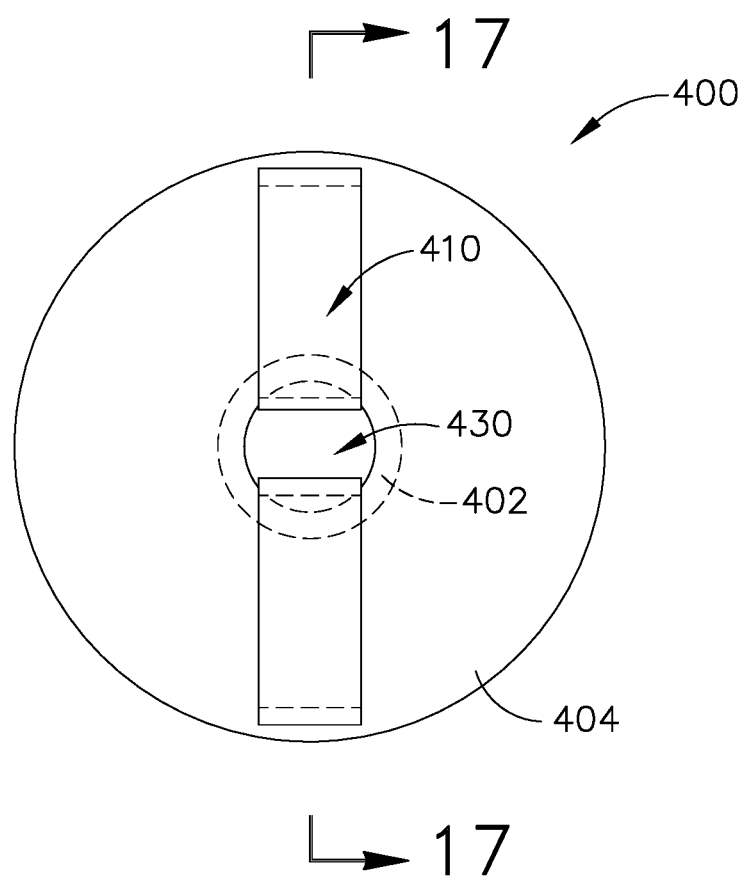
FIG. 16 depicts a rear elevational view of an exemplary implantable sinus port.
Figure 17A:
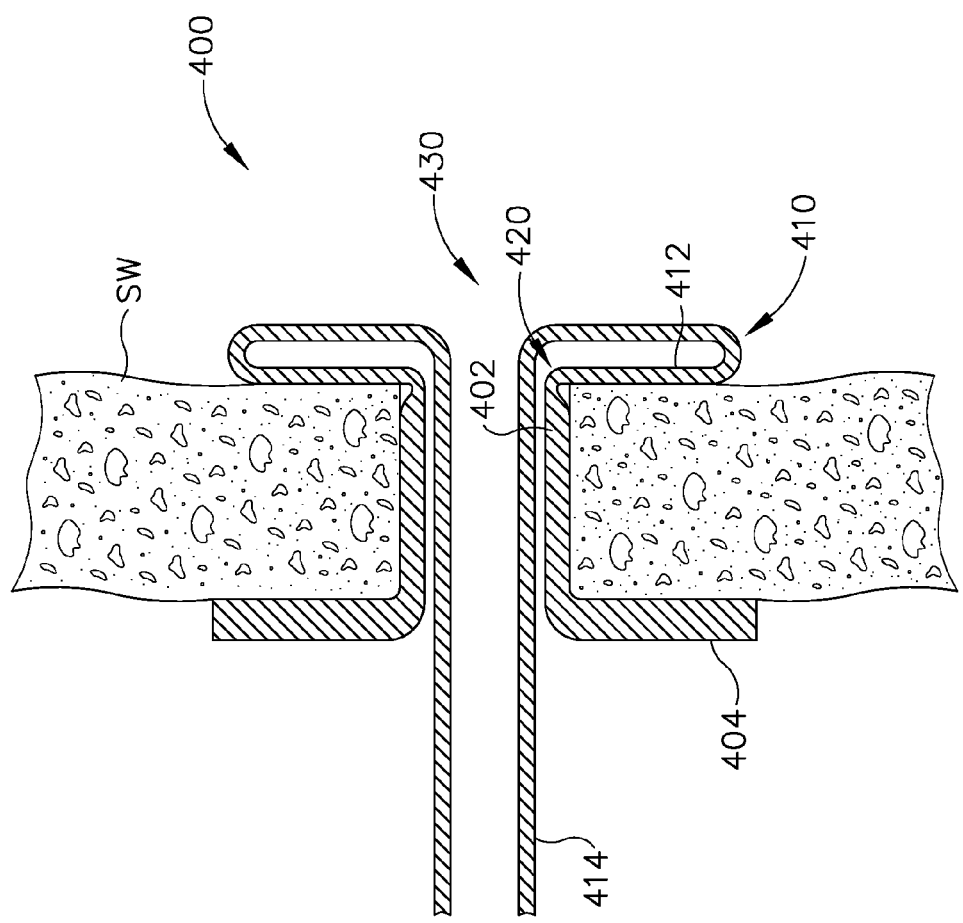
FIG. 17A depicts a cross-sectional view of the port of FIG. 16, taken along line 17-17 of FIG. 16, implanted in a sinus wall with the port in a relaxed state.
Figure 17B:
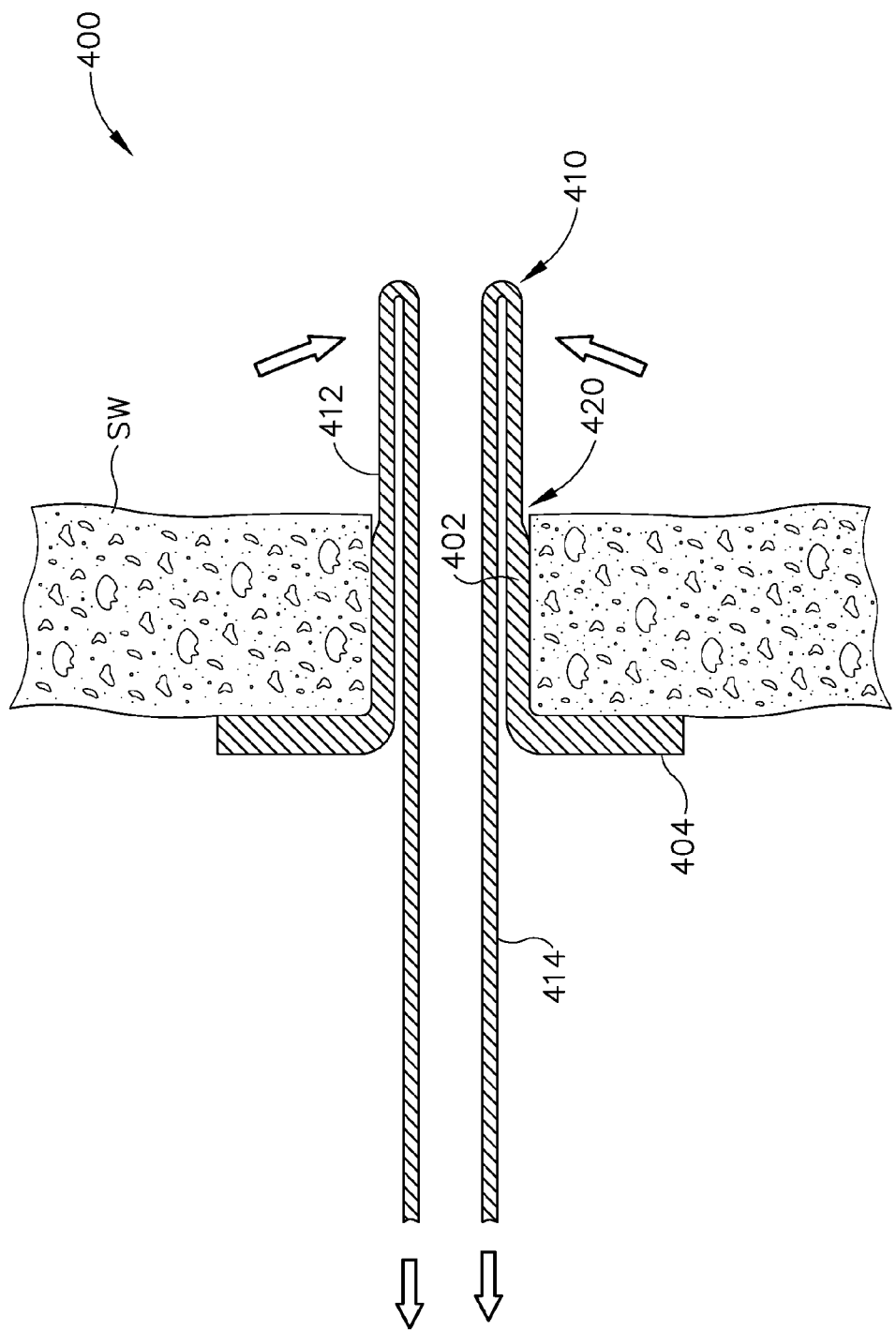
FIG. 17B depicts a cross-sectional view of the port of FIG. 16, taken along line 17-17 of FIG. 16, with retention features of the port being actuated to release the port from the sinus wall.

FIGS. 16-17B show an exemplary port (400) that includes a cylindraceous body (402), an annular flange (404), and a pair of retention wings (410). Flange (404) is resiliently biased to extend along a plane that is perpendicular to the longitudinal axis of cylindraceous body (402). Each retention wing (410) includes a strut portion (412) pivotally coupled with flange (404) by a respective living hinge (420). The material used to form living hinges (420) may have a lower flexural modulus (and be fused or otherwise molded into the remaining structure that is formed from a material of a higher flexural modulus); or may have a thinner wall and/or narrower width than strut portions (412). Port (400) defines a lumen (430) extending along the length of body (402). Each retention wing (410) includes a release element (414) extending through lumen (430). Release elements (414) extend proximal to annular flange (404), such that release elements (414) may be readily grasped from a position proximal to annular flange (404). While only two retention wings (410) are shown in the present example, it should be understood that any other suitable number of retention wings (410) may be used.

As shown in FIG. 17, port (400) may be implanted in an ostium formed in a sinus wall (SW). The ostium may be a naturally occurring ostium, a naturally occurring ostium that has been enlarged (e.g., using a balloon dilation device, etc.), or an ostium formed by an instrument. Port (400) is positioned such that retention wings (410) are located in the sinus cavity while flange (404) is located in the nasal cavity, outside the sinus cavity. Various suitable ways in which port (400) may be implanted at such positioning will be apparent to those of ordinary skill in the art in view of the teachings herein. Living hinges (420) are resiliently biased to hold retention wings (410) in the position shown in FIG. 17A. In this grommet-like configuration, wings (410) and flange 404 cooperate to hold port (400) in place in the sinus wall (SW). In particular, flange 404 prevents port (400) from migrating into the sinus cavity while retention wings (410) prevent port (400) from migrating into the nasal cavity. Lumen (430) maintains patency through the ostium in the sinus wall (SW). It should be understood that the deformability of living hinges (420), retention wings (410) and/or other features of port (400) may be varied based on wall thickness, member width, member material, and/or other factors, including combinations thereof.

In order to remove port (400) from the sinus wall (SW), the operator may simply grasp release elements (414) (e.g., using forceps, etc.), then pull release elements (414) proximally. The rigidity of strut portions (412) and the flexibility of living hinges cause retention wings (410) to pivot inwardly in response to proximal pulling on release elements (414), as shown in FIG. 17B. When pivoted inwardly, retention wings (410) are substantially aligned with (or deflected inwardly relative to) the wall of body (402), such that the distance between the outermost surfaces of strut portions (412) is less than the diameter of the ostium in the sinus wall (SW). At this stage, the operator may thus pull further proximally on port (400) to remove port from the sinus wall (SW). In some instances, this may entail simply pulling further proximally on release elements (414).

In the present example, port (400) is formed from a non-bioresorbable material (e.g., silicone, etc.). Thus, port (400) will remain in the sinus wall (SW) until it is removed. In some other versions, at least a portion of port (400) may be formed of a bioresorbable or biodegradable material, such that port (400) may eventually dislodge or disappear from the sinus wall (SW) even if it is not actively removed.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a retainer body, wherein the retainer body is configured to fit in an opening in a sinus wall; (b) an absorbent member; (c) a compression feature coupled with the body, wherein the compression feature is configured to selectively compress at least a portion of the absorbent member to thereby drive fluid from the absorbent member.

Example 2

The apparatus of Example 1, wherein the retainer body includes a first flange and a second flange.

Example 3

The apparatus of Example 2, wherein the first flange and the second flange are spaced to receive the sinus wall between the first flange and the second flange.

Example 4

The apparatus of any of the preceding Examples 1 through 3, wherein the retainer body has a cylindraceous configuration.

Example 5

The apparatus of any of the preceding examples 1 through 4, wherein the retainer body defines a fluid passageway.

Example 6

The apparatus of Example 5, wherein the compression feature is configured to selectively compress at least a portion of the absorbent member to thereby drive fluid from the absorbent member through the fluid passageway of the body.

Example 7

The apparatus of any of the preceding Examples 1 through 6, wherein the compression feature has a disc shape.

Example 8

The apparatus of any of the preceding Examples 1 through 7, wherein the absorbent member is captured between the compression feature and the retainer body.

Example 9

The apparatus of any of the preceding Examples 1 through 8, further comprising a brace coupling the compression feature with the retainer body.

Example 10

The apparatus of Example 9, wherein the brace is flexible, such that the brace enables deflection of the compression feature away from a longitudinal axis extending along a center of the retainer body.

Example 11

The apparatus of any of the preceding Examples 1 through 10, further comprising an extension projecting away from the compression feature, wherein the extension is configured to drive the compression feature away from a longitudinal axis extending along a center of the retainer body in response to a lateral force exerted on the extension.

Example 12

The apparatus of Example 11, wherein the extension comprises a paddle.

Example 13

The apparatus of Example 12, wherein the extension is configured to drive the compression feature away from a longitudinal axis extending along a center of the retainer body in response to inspired air impinging against an anterior face of the extension.

Example 14

The apparatus of any of the preceding Examples 1 through 13, wherein absorbent member comprises a foam structure.

Example 15

The apparatus of any of the preceding Examples 1 through 14, wherein the absorbent member comprises an exposed portion and a covered portion.

Example 16

The apparatus of Example 15, further comprising a non-permeable skin covering the covered portion of the absorbent member.

Example 17

The apparatus of Example 15, wherein the exposed portion is associated with an anterior side of the absorbent member.

Example 18

The apparatus of Example 15, wherein the covered portion is associated with a posterior side of the absorbent member.

Example 19

The apparatus of any of the preceding Examples 1 through 18, wherein the absorbent member is saturated with a medical liquid.

Example 20

A method of treating a sinus using an implant, wherein the implant includes a retainer body, an absorbent member, and a compression feature, wherein the compression feature is configured to selectively compress at least a portion of the absorbent member to thereby drive fluid from the absorbent member, wherein the compression feature comprises an impingement face, the method comprising: (a) positioning the retainer body in an opening in a sinus wall; and (b) orienting the retainer body such that the impingement face is facing anteriorly such that inspired air will impinge against the impingement face, wherein the compression feature is configured to drive fluid from the absorbent member in response to inspired air impinging against the impingement face.

Example 21

The method of Example 20, wherein the sinus wall comprises an ethmoid bulla sinus wall.

Example 22

The method of any of the preceding Examples 20 through 21, wherein the opening comprises a naturally occurring opening in the sinus wall.

Example 23

The method of Example 22, further comprising enlarging the naturally occurring opening in the sinus wall.

Example 24

The method of Example 23, wherein the act of enlarging comprises inflating a dilator in the naturally occurring opening.

Example 25

The method of Example 20, further comprising forming the opening in the sinus wall.

Example 26

An apparatus, comprising: (a) an absorbent body, wherein the absorbent body comprises a wicking feature; (b) a non-permeable feature coupled with the absorbent body, wherein the non-permeable feature and at least a portion of the absorbent body are configured to fit in an opening in a sinus wall; and (c) a port feature extending through the absorbent body, wherein the port feature defines a lumen.

Example 27

The apparatus of Example 26, wherein the port feature comprises a tubular structure.

Example 28

The apparatus of Example 27, wherein the tubular structure defines a longitudinal axis.

Example 29

The apparatus of Example 28, wherein the wicking feature extends obliquely relative to the longitudinal axis.

Example 30

The apparatus of any of the preceding Examples 26 through 29, wherein the wicking feature is configured to contact tissue inside a sinus cavity while the non-permeable feature is positioned in an opening formed in the wall of the sinus cavity.

Example 31

The apparatus of any of the preceding Examples 26 through 30, wherein the non-permeable feature has a grommet configuration.

Example 32

The apparatus of any of the preceding Examples 26 through 31, wherein the non-permeable feature and the port feature are coaxially aligned with each other.

Example 33

The apparatus of any of the preceding Examples 26 through 32, wherein the absorbent body further comprises a plurality of wicking features.

Example 34

The apparatus of Example 33, wherein the wicking features extend outwardly.

Example 35

The apparatus of any of the preceding Examples 26 through 34, wherein the absorbent body comprises polyvinyl alcohol foam.

Example 36

The apparatus of any of the preceding Examples 26 through 35, wherein the absorbent body passes through the non-permeable feature.

Example 37

The apparatus of Example 36, wherein the non-permeable feature comprises a sleeve, skin, film, or coating positioned about the absorbent body.

Example 38

The apparatus of any of the preceding Examples 26 through 37, wherein the absorbent body is configured to deliver fluid from a location in the nasal cavity to mucosal tissue in a sinus cavity defined by the sinus wall, through a capillary action provided by the wicking feature.

Example 39

The apparatus of any of the preceding Examples 26 through 38, wherein the lumen of the port feature is configured to provide a path for ingress of air into a sinus cavity defined by the sinus wall and egress of mucus from the sinus cavity defined by the sinus wall.

Example 40

A method of treating a sinus using an implant, wherein the implant includes an absorbent body, a non-permeable feature, and a port feature, wherein the absorbent body comprises a wicking feature, wherein the wicking feature extends obliquely relative to the port feature, the method comprising: (a) positioning the non-permeable feature in an opening in a sinus wall; and (b) orienting the absorbent body such that the wicking feature is in contact with mucosal tissue in a sinus cavity defined by the sinus wall, wherein a proximal portion of the absorbent body is positioned outside the sinus wall.

Example 41

The method of Example 40, wherein the sinus wall comprises an ethmoid bulla sinus wall.

Example 42

The method of any of the preceding Examples 40 through 41, wherein the opening comprises a naturally occurring opening in the sinus wall.

Example 43

The method of Example 42, further comprising enlarging the naturally occurring opening in the sinus wall.

Example 44

The method of Example 43, wherein the act of enlarging comprises inflating a dilator in the naturally occurring opening.

Example 45

The method of any of the preceding Examples 40 through 41, further comprising forming the opening in the sinus wall.

Example 46

The method of any of the preceding Examples 40 through 45, further comprising administering a fluid to the proximal portion of the absorbent body, wherein the wicking feature is configured to communicate the administered fluid to the mucosal tissue through a capillary action.

Example 47

An apparatus, comprising (a) an absorbent body; (b) a non-permeable feature coupled with the absorbent body, wherein the non-permeable feature is configured to fit in an opening in a sinus wall; and (c) a plurality of extensions extending outwardly from the absorbent body, wherein the extensions are configured to wick fluid from the absorbent body along the lengths of the extensions.

Example 48

The apparatus of Example 47, wherein each extension includes a respective covered portion and exposed portion.

Example 49

The apparatus of Example 48, further comprising one or more skins covering the covered portions of the extensions.

Example 50

The apparatus of Example 49, wherein the one or more skins are formed of a non permeable material.

Example 51

The apparatus of any one of the preceding Examples 48 through 50, wherein the exposed portions are located at free ends of the extensions.

Example 52

The apparatus of any one of the preceding Examples 47 through 51, wherein absorbent body is sized and configured to fit in a middle meatus of a nasal cavity.

Example 53

The apparatus of Example 52, wherein a first extension of the plurality of extensions has a free end and a length, wherein the length is configured to enable placement of the free end in a frontal recess of the nasal cavity while the absorbent body is positioned in the middle meatus of the nasal cavity.

Example 54

The apparatus of Example 52, wherein a first extension of the plurality of extensions has a free end and a length, wherein the length is configured to enable placement of the free end in a maxillary sinus while the absorbent body is positioned in the middle meatus of the nasal cavity.

Example 55

The apparatus of Example 52, wherein a first extension of the plurality of extensions has a free end and a length, wherein the length is configured to enable placement of the free end in an anterior region of the middle meatus while the absorbent body is positioned in the middle meatus of the nasal cavity.

Example 56

The apparatus of any one of the preceding Examples 47 through 55, wherein the retention feature comprises a cylindraceous body.

Example 57

The apparatus of any one of the preceding Examples 47 through 56, wherein the retention feature comprises a flange configured to fit in a sinus cavity.

Example 58

A method of treating a sinus using an implant, wherein the implant includes an absorbent body, a retention feature, and a plurality of extensions extending outwardly from the absorbent body, wherein the extensions are configured to wick fluid from the absorbent body along the lengths of the extensions, the method comprising: (a) positioning the absorbent body in a first region of the nasal cavity; (b) positioning a first extension of the plurality of extensions in a second region of the nasal cavity; and (c) orienting a second extension of the plurality of extensions in a third region of the nasal cavity.

Example 59

The method of Example 58, wherein the first region comprises a middle meatus.

Example 60

The method of Example 59, further comprising positioning a third extension of the plurality of extensions in an anterior region of the middle meatus.

Example 61

The method of Example 60, further comprising administering a fluid to the third extension, wherein the first and second extensions are configured to communicate the administered fluid to mucosal tissue in the second and third region of the nasal cavity through a capillary action.

Example 62

The method of any one of the preceding Examples 58 through 61, wherein the second region comprises a frontal recess.

Example 63

The method of any one of the preceding Examples 58 through 62, wherein the third region comprises a maxillary sinus.

Example 64

The method of any one of the preceding Examples 58 through 63, further comprising securing the retention feature to a region of the ethmoid bulla.

Example 65

An apparatus, comprising: (a) a port body defining a longitudinal axis and a lumen, wherein the port body is configured to fit in an opening formed through a sinus wall; (b) a first retaining feature located at a proximal end of the port body; (c) a second retaining feature located at a distal end of the port body; and (d) a release feature operable to selectively deflect the second retaining feature inwardly toward the longitudinal axis defined by the port body.

Example 66

The apparatus of Example 65, wherein the lumen extends along the longitudinal axis.

Example 67

The apparatus of any of the preceding Examples 65 through 66, wherein the first retaining feature comprises an outwardly extending flange.

Example 68

The apparatus of any of the preceding Examples 65 through 67, wherein the second retaining feature comprises at least two wings.

Example 69

The apparatus of any of the preceding Examples 65 through 68, wherein the second retaining feature is coupled with the port body by one or more living hinges.

Example 70

The apparatus of any of the preceding Examples 65 through 69, wherein the second retaining feature is resiliently biased to extend outwardly relative to the longitudinal axis defined by the port body.

Example 71

The apparatus of any of the preceding Examples 65 through 70, wherein the release feature extends through the lumen of the port body.

Example 72

The apparatus of any of the preceding Examples 65 through 71, wherein the release feature is accessible from a location proximal to the first retaining feature.

Example 73

The apparatus of any of the preceding Examples 65 through 72, wherein the release feature is operable to deflect the second retaining feature inwardly in response to proximal movement of the release feature relative to the port body.

Example 74

A method of treating a sinus using an apparatus comprising a port body, a first retaining feature, a second retaining feature, and a release feature, wherein the port body defines a longitudinal axis and a lumen, wherein the first retaining feature is located at a proximal end of the body, wherein the second retaining feature is located at a distal end of the port body, wherein the release feature is feature operable to selectively deflect the second retaining feature inwardly toward the longitudinal axis defined by the port body, the method comprising: (a) passing the second retaining feature through an opening formed in a sinus wall; and (b) positioning the port body in the opening formed through the sinus wall such that the sinus wall is positioned between the first and second retaining features.

Example 75

The method of Example 74, wherein the sinus wall comprises an ethmoid bulla sinus wall.

Example 76

The method of any of the preceding Examples 74 through 75, wherein the opening comprises a naturally occurring opening in the sinus wall.

Example 77

The method of Example 76, further comprising enlarging the naturally occurring opening in the sinus wall.

Example 78

The method of Example 77, wherein the act of enlarging comprises inflating a dilator in the naturally occurring opening.

Example 79

The method of any of the preceding Examples 74 through 75, further comprising forming the opening in the sinus wall.

Example 80

The method of any of the preceding Examples 74 through 79, wherein the act of passing the second retaining feature through an opening formed in a sinus wall comprises deflecting the second retaining feature inwardly toward the longitudinal axis defined by the port body.

Example 81

The method of Example 80, further comprising releasing the second retaining feature to enable the second retaining feature to deflect away from the longitudinal axis defined by the port body.

Example 82

The method of any of the preceding Examples 74 through 81, further comprising pulling proximally on the release feature to deflect the second retaining feature toward the longitudinal axis defined by the port body.

Example 83

The method of Example 82, wherein the second retaining feature is substantially aligned with the port body in response to the act of pulling proximally on the release feature.

V. MISCELLANEOUS

The various devices described herein may be used in various anatomical locations in addition to or in lieu of those locations described herein. By way of example only, the devices described herein may be used in an opening that is surgically formed in a paranasal sinus wall, a naturally occurring opening in a paranasal sinus wall, a naturally occurring opening that has been surgically altered in a paranasal sinus wall, other kinds of drainage passageways or outflow tracts of the various paranasal sinuses, and/or other locations. Various suitable locations in which the devices described herein may be used will be apparent to those of ordinary skill in the art in view of the teachings herein. Similarly, various clinical contexts in which the devices described herein may be used will be apparent to those of ordinary skill in the art in view of the teachings herein.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A sinus wall implant comprising:
   (a) a cylindraceous body defining a longitudinal axis and a lumen;
   (b) a flange extending from a first side of the cylindraceous body, wherein the flange is resiliently biased to extend along a plane perpendicular to the longitudinal axis of the cylindraceous body;
   (c) a retention wing extending from a second side of the cylindraceous body; and
   (d) a release element extending from the retention wing through the lumen.

2. The sinus wall implant of claim 1, wherein the retention wing comprises a living hinge, wherein the living hinge connects the retention wing to the cylindraceous body.

3. The sinus wall implant of claim 2, wherein the retention wing comprises a strut, wherein the living hinge connects the strut to the cylindraceous body.

4. The sinus wall implant of claim 3, wherein the strut comprises a strut wall having a width, wherein the living hinge comprises a hinge wall having a width, wherein the width of the strut wall is greater than the width of the hinge wall.

5. The sinus wall implant of claim 3, wherein the strut has a flexural modulus, wherein the living hinge has a flexural modulus, wherein the flexural modulus of the strut is greater than the flexural modulus of the living hinge.

6. The sinus wall implant of claim 1, wherein the flange is configured to abut a sinus wall within a nasal cavity of a patient.

7. The sinus wall implant of claim 6, wherein the retention wing is configured to abut a sinus wall within a sinus cavity of the patient.

8. The sinus wall implant of claim 7, wherein the retention wing is disposed at a distal end of the cylindraceous body, wherein the flange is disposed at a proximal end of the cylindraceous body, and wherein the release element extends proximal to the flange.

9. The sinus wall implant of claim 7, wherein the flange comprises a first side and an opposed second side, wherein the release element extends from the first side to the second side and parallel to the longitudinal axis.

10. The sinus wall implant of claim 7, wherein the sinus wall implant is operable to transition between a first position and a second position, wherein the retention wing comprises a strut, wherein the release element and the strut are perpendicular in the first position, wherein the release element and the strut are parallel in the second position.

11. The sinus wall implant of claim 1, wherein the flange is annular.

12. The singular wall implant of claim 1, wherein the singular wall implant is formed from a non-bioresorbable material.

13. The singular wall implant of claim 1, wherein the singular wall implant is formed from a bioresorbable material.

14. A method of treating a patient using a sinus wall implant, wherein the sinus wall implant comprises a cylindraceous body defining a longitudinal axis, defining a lumen through the longitudinal axis, a flange extending from a first side of the cylindraceous body, and a pair of retention wings extending from a second side of the cylindraceous body, and a release element extending from the retention wings and through the lumen the method comprising:
   (a) locating an opening formed in a sinus wall, wherein the opening extends between a nasal cavity and a sinus cavity;
   (b) passing the pair of retention wings from the nasal cavity through the opening to the sinus cavity;
   (c) abutting the pair of retention wings with the sinus wall after the pair of retention wings pass through the opening;
   (d) positioning the flange in the nasal cavity;
   (e) abutting the flange with the sinus wall; and
   (f) disposing the release element in the opening when the retention wings are disposed in the sinus cavity.

15. The method of claim 14, further comprising pulling the release element through the opening and into the nasal cavity to remove the pair of retention wings from the sinus cavity.

16. The method of claim 15, further comprising rotating each retention wing in the pair of retention wings about a living hinge in response to pulling the release element.

17. The method of claim 14, further comprising orienting the pair of retention wings parallel to the longitudinal axis to pass the retention wings pass through the opening.

18. An apparatus for placement within a sinus wall, the apparatus comprising:
   (a) a cylindraceous body defining a longitudinal axis and a lumen extending along the longitudinal axis;
   (b) a flange;
   (c) a retention wing, wherein the retention wing is configured to rotate between a first position and a second position, wherein the retention wing is parallel to the longitudinal axis in the first position, wherein the retention wing is perpendicular to the longitudinal axis in the second position; and
   (d) a release element, wherein the release element that extends from the retention wings and is configured to be disposed in the lumen when the retention wing is in the second position.

19. The apparatus of claim 18, further comprising a living hinge connecting the retention wing to the cylindraceous body.

20. The apparatus of claim 18, further comprising a retention element disposed in the lumen and extending from the retention wing.

* * * * *